US006521411B2

(12) United States Patent
Hecker et al.

(10) Patent No.: US 6,521,411 B2
(45) Date of Patent: Feb. 18, 2003

(54) METHOD AND SYSTEM FOR THE PREPARATION OF CDNA

(75) Inventors: Karl H. Hecker, Milpitas, CA (US);
Arezou Azarani, San Jose, CA (US);
David Hornby, Cheshire (GB);
Christopher P. Hanna, Greenfield, MA (US); Douglas T. Gjerde, Saratoga, CA (US); Maryam Matin, Sheffield (GB)

(73) Assignee: Transgenomic, Inc., San Jose, CA (US)

( * ) Notice: Subject to any disclaimer, the term of this patent is extended or adjusted under 35 U.S.C. 154(b) by 0 days.

(21) Appl. No.: 09/808,447

(22) Filed: Mar. 13, 2001

(65) Prior Publication Data

US 2002/0062017 A1 May 23, 2002

Related U.S. Application Data

(60) Provisional application No. 60/236,398, filed on Sep. 28, 2000, provisional application No. 60/250,306, filed on Nov. 29, 2000, and provisional application No. 60/256,050, filed on Dec. 15, 2000.

(51) Int. Cl.[7] .......................... C12Q 1/68; C07H 21/02; C07H 21/04
(52) U.S. Cl. ......................... 435/6; 536/23.1
(58) Field of Search .............................. 435/6; 536/23.1

(56) References Cited

U.S. PATENT DOCUMENTS

| | | | |
|---|---|---|---|
| 4,563,510 A | 1/1986 | Ugelstad | |
| 4,906,378 A | 3/1990 | Hagen et al. | |
| 5,334,310 A | 8/1994 | Frechet et al. | |
| 5,338,448 A | 8/1994 | Gjerde | |
| 5,438,128 A | 8/1995 | Nieuwkerk et al. | |
| 5,453,185 A * | 9/1995 | Frechet et al. | 210/198.2 |
| 5,522,994 A | 6/1996 | Frechet et al. | |
| 5,585,236 A | 12/1996 | Bonn et al. | |
| 5,772,889 A | 6/1998 | Gjerde et al. | |
| 5,945,515 A | 8/1999 | Chomczynski | |
| 5,972,222 A | 10/1999 | Gjerde et al. | |
| 5,973,137 A | 10/1999 | Heath | |
| 5,986,085 A | 11/1999 | Gjerde et al. | |
| 5,997,742 A | 12/1999 | Gjerde et al. | |
| 6,017,457 A | 1/2000 | Gjerde et al. | |
| 6,030,527 A | 2/2000 | Gjerde et al. | |
| 6,056,877 A | 5/2000 | Gjerde et al. | |
| 6,066,258 A | 5/2000 | Gjerde et al. | |
| 6,174,441 B1 | 1/2001 | Gjerde et al. | |
| 6,177,559 B1 | 1/2001 | Gjerde et al. | |
| 6,238,565 B1 * | 5/2001 | Hatch | 210/635 |
| 6,251,272 B1 | 6/2001 | Gjerde et al. | |
| 6,265,168 B1 | 7/2001 | Gjerde et al. | |
| 6,355,791 B1 | 3/2002 | Gjerde et al. | |

FOREIGN PATENT DOCUMENTS

| | | | | |
|---|---|---|---|---|
| WO | WO 98/48913 | * 11/1998 | ........... | B01D/15/00 |
| WO | WO 98/48914 | 11/1998 | | |
| WO | WO 98/56797 | 12/1998 | | |
| WO | WO 98/56798 | * 12/1998 | ........... | C07H/1/00 |
| WO | WO 01/66218 | 9/2001 | | |
| WO | WO 01/81566 | 11/2001 | | |

OTHER PUBLICATIONS

Van der Mast, C. a. et al., "Separation of translationally active mRNAs by reversed–phase ion–pair high–performance liquid chromatography", J. Chromatogr., vol. 564, pp. 115–125 (1991).*
U.S. patent application Ser. No. 09/469,551, Gjerde et al., filed Dec. 22, 1999.
U.S. patent application Ser. No. 09/557,424, Gjerde et al., filed Apr. 21, 2000.
U.S. patent application Ser. No. 09/753,856, Gjerde et al., filed Jan. 2, 2001.
U.S. patent application Ser. No. 09/764,041, Gjerde et al., filed Jan. 16, 2001.
U.S. patent application Ser. No. 09/802,466, Taylor et al., filed Mar. 9, 2001.
U.S. patent application Ser. No. 09/809,867, Hornby et al., filed Mar. 15, 2001.
U.S. patent application Ser. No. 09/826,055, Gjerde et al., filed Apr. 3, 2001.
U.S. patent application Ser. No. 09/912,568, Taylor et al., filed Jul. 24, 2001.
U.S. patent application Ser. No. 10/126,055, Gjerde et al., filed Apr. 18, 2002.
AbouHaidar et al, Non–Enzymatic RNA Hydrolysis Promoted By The Combined Catalytic Activity of Buffers and Magnesium Ions, Z. Naturforsch 54[C]:542–548 (1999).
Arends et al., Partial Purification and Characterization of Nuclear Ribonuclease P From Wheat, Eur J. Biochem. 244:635–645 (1997).
Azarani A, et al., RNA Analysis By Ion–Pair Reversed–Phase HPLC Proceedings of the 2000 Miami Nature Biotechnology Winter Symposium, Miami Nature Biotechnology Short Reports, Oxford University Press, 11:29 (2000).
Bischoff et al, Isolation of Specific tRNAs Using An Ionic–Hydrophobic Mixed–Mode Chromatographic Matrix, Analytical Biochemistry, 151:526–533 (1985).

(List continued on next page.)

Primary Examiner—Kenneth R. Horlick
Assistant Examiner—Teresa Strzelecka

(57) ABSTRACT

In one aspect, the present invention concerns an improved method for the preparation of cDNA libraries. Preferred embodiments of the invention include methods and systems capable of generating cDNA libraries enriched for high molecular weight cDNA inserts. The method generally entails the following steps: (1) size-based separation of a plurality of mRNA molecules by Ion-Pairing Reversed-Phase Chromatography (IP-RPC), preferably using HPLC under denaturing conditions; and (2) collection of a fraction of the mRNA molecules that is enriched for mRNA molecules of a desired size range (in a preferred embodiment of the invention, larger-sized mRNA molecules are collected, e.g., mRNA of length greater than 10 kb). The collected fraction of mRNA molecules can be reverse transcribed to form a library of cDNA inserts enriched for inserts of a desired relative size range.

34 Claims, 5 Drawing Sheets

OTHER PUBLICATIONS

Bishop et al., Conformational Effects of Reversed–Phase HPLC on Ribonuclease A and x–Chymotrypsin By Prarticle Beam LC/FT–IR Spectrometry, Mikrochim. Actu [Suppl.] 14:721–724 (1997).

Chomczynski et al., Single–Step Method of RNA Isolation By Acid Guanidinium Thiocyanate–Phenol–Chloroform Extraction, Anal. Biochem. 162:156–159 (1987).

Djordjevic et al., HPLC Separation of Oligonucleotides In Isocratic and Temperature–Programming Mode, Analytical Chemistry, 70:1921–1925 (1998).

Dolezal et al., Micropreparative Separation of Transfer Ribonucleic Acids By High–Performance Liquid Chromatography, Journal of Chromatography, 463:409–417 (1989).

Garcia et al., Behaviour of Macromolecular RNA In Reversed–Phase HPLC, Journal of Chrom. Science, 21:398–404 (1983).

Georgopoulos et al., Use of High–Performance Liquid Chromatographic Fractionation By Large RNA Molecules In The Assay of Group I Intron Ribozyme Activity, Journal of Chrom. A, 868:109–114 (2000).

Hayward–Lester et al., Rapid Quantification of Gene Expression By Competitive RT–PCR and Ion–Pair Reversed–Phase HPLC, BioTechniques, 20:250–257 (1996).

Hayward–Lester et al., Modeling And Analysis Of Competitive RT–PCR, Nucleic Acids Res., 26:2511–2518 (1998).

Hecker, K., et al., Optimization of Cloning Efficacy By Pre–Cloning DNA Fragment Analysis, BioTechniques, 26:216–218 (1999).

Huber et al, Rapid Analysis of Biopolymers on Modified Non–Porous Polystyrene–Divinylbenzene Particles, Chromatographia, 37:653–658, (1993).

Huber et al, High–Resolution Liquid Chromatography of Oligonucleotides on Nonporous Alkylated Styrene–Divinylbenzene Copolymers, Analytical Biochemistry, 212:351–358 (1993).

Huber et al, Rapid and Accurate Sizing of DNA Fragments By Ion–Pair Chromatography on Alkylated Nonporous Poly(Styrene–Divinylbenzene) Particles, Analytical Chemistry, 67:578–585 (1995).

Kanuc, Fractionation of Rat Liver tRNA By Reversed–Phase High Performance Liquid Chromatography: Isolation of ISO–tRNAs, Preparative Biochemistry, 24:167–174 (1994).

Klink et al, Contribution of Disulfide Bonds To The Conformational Stability and Catalytic Activity of Ribonuclease A, Eur. J. Biochem. 267:566–572 (2000).

Kuklin et al., Detection of Single–Nucleotide Polymorphisms with The Wave(™) DNA Fragment Analysis Sytem, Genetic Testing, vol. 1 No. 3:201–206 (1997).

Kuklin et al., A Novel Technique For Rapid Automated Genotyping of DNA Polymorphisms In The Mouse, Mol. Cell Probes, 13:239–242 (1999).

Kwiatkowski et al., Use of Reverse Phase Ion Pair Chromatography To Fractionate and Purify DNA Fragments and Monomeric Components of RNA, Acta. Chem. Scandinavica B., 38:721–733 (1984).

Lalioti et al, Purification and Characterization of A Novel Poly (U), Poly (C) Ribonuclease From *Saccharomyces cerevisiae*, Biochimica et Biophysica Acta 1342:62–72 (1997).

Matsumura et al., Enormously Fast RNA Hydrolysis By Lanthanide (III) Ions Under Physiological Conditions: Eminent Candidates For Novel Tools of Biotechnology, J. Biochem., 122:387–394 (1997).

McFarland et al., Separation of Oligo–RNA By Reverse–Phase HPLC, Nucleic Acids Research, 7:1067–1080 (1979).

O'Donovan et al., Blind Analysis of Denaturing High–Performance Liquid Chromatography As A Tool For Mutation Detection, Genomics, 52:44–49 (1998).

Oefner et al., Allelic Discrimination By Denaturing High–Performance Liquid Chromatography, J. Chromatography, 739:345–355 (1994).

Pager, A Liquid Chromatpgraphic Preparation of Retroviral RNA, Anal. Biochem., 215:231–235 (1993).

Petro et al, Molded Monolithic Rod of Macroprous Poly(Styrene–Co–Divinylbenzene) As A Separation Medium For HPLC of Synthtic Polymers..., Analytical Chemistry, 68:315–321 (1996).

Robinson et al., Quantification of Alternatively Spliced Rush mRNA Insoforma By QRT–PCR And IP–RP–HPLC Analysis: A New Approach To Measuring Regulated Splicing Efficiency, Gene, 198:1–4 (1997).

Sambrook et al, Molecular Cloning, A Laboratory Manual, $2^{nd}$ Edition, Cold Spring Harbor Laboratory Press, Chapters 7 and 8 (1989).

Sugimoto et al, Experimental Quantitation of Cation Effect of Nucleic Acid Stability, Nucleic Acids Symposium Series, 37:147–148 (1997).

Rauhut et al., mRNA Degradation In Bacteria, FEMS Microbiology Reviews, 23:353–370 (1999).

Tanaka et al, High Resolution Chromatography of Ribonucleosides and Its Application To RNA Analysis, Biomedical Chromatography, vol. 3, No. 6, (1989).

Wagner et al., Denaturing High–Performance Liquid Chromatography Detects Reliably BRCA1 and BRCA2 Mutations, Genomics, 62:369–376 (1999).

Wang et al, Reversed–Phase Chromatography of Small Molecules and Peptides on A Continous Rod of Macrophorous Poly(Styrene–Codivinylbenzene), Journal of Chromatography, 669:230–235 (1994).

Wilcox et al., Construction of a cDNA Library From Microdissected Guinea Pig Organ of Corti, Heares Res. 62: 124–126 (1992).

Wilcox et al., Construction of cDNA Library From Microdissected Guinea Pig Crista Ampullaris Heares Res. 73:65–66 (1994).

Wincott et al., Synthess, Deprotection, Analysis and Purification of RNA and Robozymes, Nucleic Acids Research, No. 14, 23:2677–2684 (1995).

Promega, RNA Applications Guide, Chapters 1 (Prevention of RNA Degradation) and 2 (RNA Purification), downloaded from www.promega.com on Jun. 4, 2001.

Working With RNA, Ambion Technical Bulletin 159, downloaded from www.ambion.com on Jun. 4, 2001.

Nuclease and Protease Testing: Laboratory and Commercial Considerations, Ambion Technical Bulletin 166, downloaded from www.ambion.com on Jun. 4, 2001.

RNAse and DEPC Treatment: Fact or Laboratory Myth, Ambion Technical Bulletin 178, downloaded from www.ambion.com on Jun. 4, 2001.

How To Maintain An RNASE–free Lab, Ambion Technical Bulletin 180, downloaded from www.ambion.com on Jun. 4, 2001.

Qiagen RNA/DNA Handbook, Nov. 1998, downloaded from www.qiagen.com on Jun. 4, 2001.

RNeasy® Midi/Maxi Handbook, Oct. 1999, downloaded from www.qiagen.com on Jun. 4, 2001.

RNeasy® Protect and RNAlater™ Handbook, Aug. 2000, downloaded from www.qiagen.com on Jun. 4, 2001.

* cited by examiner

METHOD AND SYSTEM FOR THE PREPARATION OF CDNA

CROSS REFERENCE TO RELATED CO-PENDING APPLICATIONS

This application claims priority from the following co-pending, commonly assigned provisional applications, each filed under 35 U.S.C. §111 (b):

U.S. Provisional Application No. 60/236,398, filed Sep. 28, 2000;

U.S. Provisional Application No. 60/250,306 , filed Nov. 29, 2000; and

U.S. Provisional Application No. 60/256,050, filed Dec. 15, 2000.

FIELD OF THE INVENTION

The present invention is directed to improved methods and systems for preparing cDNA molecules, especially in the form of cDNA libraries. Preferred embodiments of the invention include methods and systems capable of generating cDNA libraries enriched for high molecular weight cDNA inserts.

BACKGROUND OF THE INVENTION

With the various genome projects in the process of completion, the field of functional genomics is currently faced with the challenge of first identifying genes and then identifying the function of the different proteins encoded by these genes. The human genome is estimated to contain about 100,000 genes (Borrebaeck, C. A. (1998) *Immunol. Today* 19: 524–7). Therefore, the main focus in the forthcoming era will be on identification of the role of these genes in normal and disease states. This will consequently result in the design of more effective treatments. Novel, automated, high-capacity, and reliable technologies have to be developed to ensure the success of this complex task. This includes the invention and development of easier and faster methods of RNA isolation, purification, reverse transcription, cDNA library construction and screening, gene expression, translation, and protein purification, as well as mutation detection. The instant invention represents such a method.

SUMMARY OF THE INVENTION

In one aspect, the present invention concerns an improved method for the preparation of cDNA libraries. Preferred embodiments of the invention include methods and systems capable of generating cDNA libraries enriched for high molecular weight cDNA inserts.

In one embodiment, the invention provides a method for preparing a fraction of mRNA molecules suitable for use in the production of a cDNA library enriched for inserts of a desired relative size range comprising the steps of applying a plurality of mRNA molecules to a separation medium having a non-polar surface in the presence of a counterion agent, wherein said plurality of mRNA molecules comprises mRNA molecules of diverse sizes; eluting at least a portion of the plurality of mRNA molecules from the separation medium by means of a mobile phase that includes a solvent that is less polar than water, whereby the plurality of mRNA molecules is fractionated in a manner that is at least partially dependent upon mRNA size; and collecting a fraction of mRNA molecules as it elutes from the column, wherein the fraction of mRNA molecules collected is enriched for mRNA molecules of a desired size range relative to the plurality of mRNA molecules applied to the column, such that the fraction of mRNA molecules collected is suitable for use in the production of a cDNA library enriched for inserts of a desired relative size range.

In another embodiment, the invention provides a method for preparing a cDNA library enriched for inserts of a desired relative size range comprising the steps of: applying a plurality of mRNA molecules to a separation medium having a non-polar surface in the presence of a counterion agent, wherein said plurality of mRNA molecules comprises mRNA molecules of diverse sizes; eluting at least a portion of the plurality of mRNA molecules from the separation medium by applying a mobile phase that includes a solvent that is less polar than water, whereby the plurality of mRNA molecules is fractionated in a manner that is at least partially dependent upon mRNA size; collecting a fraction of mRNA molecules as it elutes from the column, wherein the fraction of mRNA molecules collected is enriched for mRNA molecules of a desired size range relative to the plurality of mRNA molecules applied to the column; and reverse transcribing the collected fraction of mRNA molecules to form a library of cDNA inserts enriched for inserts of a desired relative size range.

In a preferred embodiment of the invention, the fraction of mRNA molecules collected is enriched for the larger-size constituents of the plurality of mRNA molecules applied to the separation medium.

In another preferred embodiment, the library of cDNA inserts comprises cDNA inserts residing in nucleic acid vectors, such as plasmids and phage vectors, which are preferably maintained in host cells.

In another preferred embodiment, the plurality of mRNA molecules applied to the separation medium comprises a sample of total RNA or total mRNA from a biological sample.

In yet another preferred embodiment, the separation of mRNA molecules is achieved by Ion Pairing Reversed Phase HPLC. Alternatively, the separation of mRNA molecules can be achieved in a batch process, for example by use of an apparatus selected from the group consisting of spin columns, vacuum tray devices low pressure columns and medium pressure columns.

In a preferred embodiment of the invention, the separation of mRNA molecules is achieved under denaturing conditions. mRNA denaturation can be achieved by conducting the separation at a temperature sufficient to denature at least some portion of the plurality of mRNA molecules applied to the separation medium, by conducting the separation in the presence of a chemical denaturant, or by conducting the separation at a pH sufficient to denature at least some portion of the plurality of mRNA molecules applied to the separation medium.

Preferably the separation of mRNA molecules is conducted at a temperature greater than about 50° C., more preferably at a temperature of about 75° C. or greater.

The separation is preferably conducted under conditions that are substantially free of multivalent cations capable of interfering with polynucleotide separations.

In a preferred embodiment of the invention, the separation medium comprises particles selected from the group consisting of silica, silica carbide, silica nitrite, titanium oxide, aluminum oxide, zirconium oxide, carbon, insoluble polysaccharide, and diatomaceous earth, the particles having separation surfaces which are coated with a hydrocarbon or non-polar hydrocarbon substituted polymer, or have substantially all polar groups reacted with a non-polar hydrocarbon or substituted hydrocarbon group, wherein the surfaces are non-polar.

In another embodiment, the separation medium comprises polymer beads having an average diameter of 0.5 to 100 microns, the beads being unsubstituted polymer beads or polymer beads substituted with a moiety selected from the group consisting of hydrocarbon having from one to 1,000,000 carbons. A particularly preferred separation medium comprises C-18 alkylated nonporous poly(styrene-divinylbenzene) polymer beads.

In another embodiment, the separation medium comprises a monolith.

In a preferred embodiment of the invention, the separation medium is substantially free of multivalent cations capable of interfering with polynucleotide separations. The separation medium is preferably prepared using reagents that are substantially free of multivalent cations capable of interfering with polynucleotide separations and under conditions that are substantially free of multivalent cations capable of interfering with polynucleotide separations.

In a preferred embodiment of the invention, the separation medium has been subjected to acid wash treatment to remove any residual surface metal contaminants and/or subjected to treatment with a multivalent cation-binding agent.

In a preferred embodiment of the invention, the mobile phase includes an organic solvent selected from the group consisting of alcohol, nitrile, dimethylformamide, tetrahydrofuran, ester, ether, and mixtures of one or more thereof, where acetonitrile is particularly preferred.

In another preferred embodiment of the invention, the mobile phase includes a counterion agent selected from the group consisting of lower alkyl primary amine, lower alkyl secondary amine, lower alkyl tertiary amine, lower trialkylammonium salt, quaternary ammonium salt, and mixtures of one or more thereof. Particularly preferred is the use of a counterion agent selected from the group consisting of octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyidiethylammonium acetate, butylethylammonium acetate, methylhexylammonium acetate, tetramethylammonium acetate, tetraethylammonium acetate, tetrapropylammonium acetate, dimethydiethylammonium acetate, triethylammonium acetate, tripropylammonium acetate, tributylammonium acetate, tetrapropylammonium acetate, tetrabutylammonium acetate, triethylammonium hexafluoroisopropyl alcohol, and mixtures of one or more thereof, of which tetrabutylammonium bromide and triethylammonium acetate are especially preferred.

DETAILED DESCRIPTION OF THE INVENTION

Figure 1:
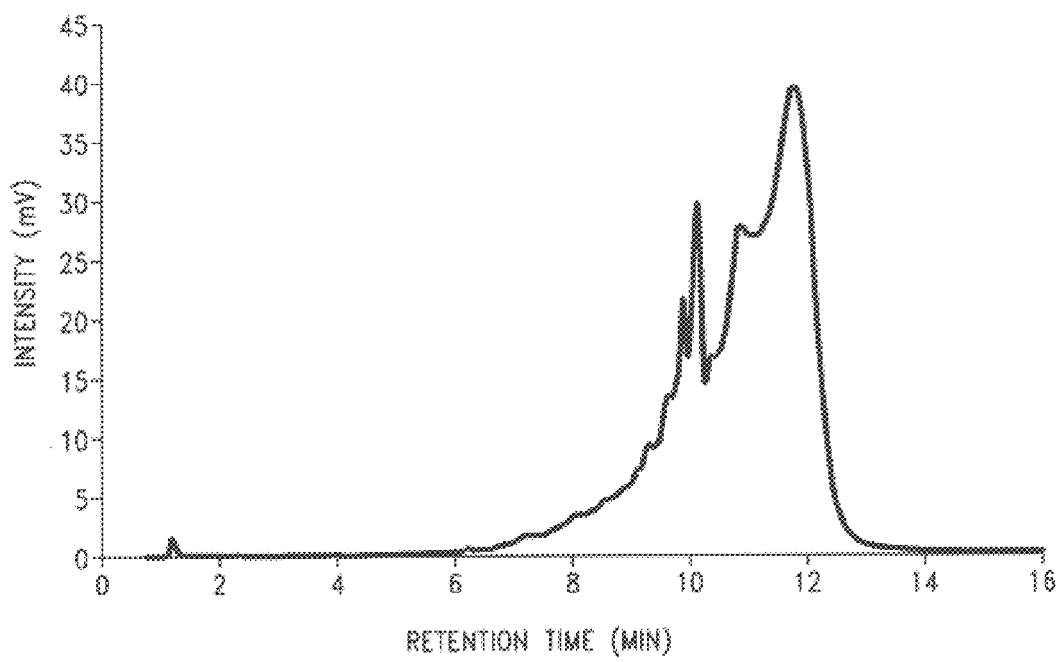
FIG. 1 is a chromatogram representing mRNA fractionation by IP-RP-HPLC, as described in Example 1.

The method of the invention generally entails the following steps: (1) size-based separation of a plurality of mRNA molecules by Ion-Pairing Reversed-Phase Chromatography (IP-RPC), preferably under denaturing conditions; and (2) collection of a fraction of the mRNA molecules that is enriched for mRNA molecules of a desired size range (in a preferred embodiment of the invention, larger-sized mRNA molecules are collected, e.g., mRNA of length greater than 10 kb). The collected fraction of mRNA molecules can be reverse transcribed to form a library of cDNA inserts enriched for inserts of a desired relative size range. The method is described in more detail below.

As used herein, the term "cDNA insert" refers to a fragment of cDNA, normally double stranded, that is derived from an RNA template by reverse transcription. A cDNA insert will often, but need not necessarily, reside in a nucleic acid vector (e.g., a plasmid, phage, etc.). A cDNA insert can represent a full length mRNA molecule, or some fraction of an mRNA molecule.

The term "cDNA library" refers to a collection of cDNA inserts, normally prepared by reverse transcription of a sample of mRNA. The cDNA inserts can take the form of linear fragments of DNA, or, more typically, will reside as inserts in a nucleic acid vector. The members of the cDNA library can, but need not necessarily, be maintained and propagated in a host cell.

In general, a cDNA library will comprise cDNA inserts of diverse sizes, reflecting the diverse sizes of the mRNA molecules that were used to prepare the library. Using the process of the instant invention, it is possible to generate a cDNA library "enriched for inserts of a desired relative size range." The term "relative size range" is used to describe the range in sizes of a sub-population of cDNA inserts or mRNA molecules with reference to the range in sizes of molecules in the cDNA or mRNA population as a whole. For example, relative size ranges of small, medium and large might be used to characterize molecules falling roughly within the small, medium and large thirds of the population as a whole. For purposes of illustration, a population of cDNA inserts (or mRNA molecules) ranging in size up to greater than 10 kbases might be divided into small, medium and large size ranges that might be defined as cDNAs up to 1000 bases, between 1000 and 5000 bases, and greater than 5000 bases, respectively. In a corresponding cDNA library (or pool of mRNA) that is enriched for larger-size constituents (the desired relative size), the amount of cDNAs (or mRNAs) of greater than about 5000 bases as a proportion of the total population of the library will be greater than found in the reference population.

The instant invention employs IP-RPC to fractionate mRNA molecules in a "manner that is at least partially dependent upon mRNA size." It is to be understood that the separation need not be totally size dependent; as discussed below, the retention time of mRNA is in general a function of not only the size of the molecule, but also to some extent the chemical properties, i.e., the sequence of the molecule.

Nevertheless, an IP-RPC separation conducted as described herein will result in substantial size-based separation of a pool of mRNA molecules, and will thus allow for the production of a pool of mRNAs enriched for molecules of a desired relative size range and suitable for production of a cDNA library according to the method of the invention.

The term "denaturing conditions" refers to conditions where polynucleotides of interest (normally mRNA molecules on the context of the instant invention) are denatured, resulting in substantial loss of secondary structure and/or tertiary structure. Denaturing conditions can be achieved, for example, by conducting chromatography at high temperature (usually at about 50° C. or greater, preferably at about 50° C. or greater, and most preferably at about 75° C. or greater), at a pH sufficient to cause denaturation, in the presence of a chemical denaturant, or a combination thereof. Normally, extreme pH is not a preferred means of achieving denaturation owing to the instability of RNA under both acid and base conditions.

RNA molecules for use in the disclosed method can be prepared using known methods for preparing cellular extracts and for purifying RNA. Methods for preparing extracts containing RNA molecules are described in, for example, Sambrook et al., and Ausubel et al. Preferably the starting population of mRNA molecules is substantially full length. One suitable RNA isolation protocol is a single-step method that uses guanidine isothiocyanate/acidic phenol (Chomczynski and Sacchi (1987) *Anal. Biochem.* 162:156). The TRIZOL® Reagent method is an improvement on this single-step method that can be used to isolate high quality, undegraded RNA from various cells and tissues (Chomczynski (1993) *Biotechniques* 15:532).

One method for preparing mRNA from total RNA is by means of oligo-dT chromatography, as described, for example, by Sambrook et al. and Ausubel et al. Spin columns containing beads coated with poly-T oligomers are useful in this regard (e.g., Poly(A)Pure™ mRNA Purification Kit, Ambion, Inc., Austin, Tex.; Oligotex™ mRNA Purification System, Qiagen, Inc., Valencia, Calif.). Alternatively, mRNA can be purified from total RNA by means of IP-RPC, as described in U.S. patent application Ser. No. 09/557,424.

In handling and storing RNA it is important to maintain conditions under which the RNA is stable. RNA isolated from RNase-rich samples, such as the pancreas, may need to be stored in formamide to maintain high quality RNA, due to the carry-over of trace amounts of RNase. This is especially true for long term storage. One way to increase the stability of stored RNA samples is to dissolve the RNA in deionized formamide and store at −70° C. When ready to use, precipitate the RNA by adding NaCl to 0.2 M, followed by four volumes of ethanol. Incubate 3 to 5 min at room temperature and centrifuge at 10,000×g for 5 minutes. In addition, various RNase inhibitors can be used. As described below and in U.S. Provisional Patent Application No. 60/187,974, IP-RPC can also be used to stabilize RNA.

Ion-Pairing Reversed-Phase Chromatography (IP-RPC) is a powerful form of chromatography used in the separation and analysis of polynucleotides, including DNA (both single and double stranded) and RNA (Eriksson et al., (1986) *J. Chromatography* 359:265–74). Most reported applications of IP-RPC have been in the context of high performance liquid chromatography (IP-RP-HPLC), but the technology can be accomplished using non-HPLC chromatography systems (U.S. patent application Ser. Nos. 09/318,407 and 09/391,963. Nevertheless, for the sake of simplicity much of the following description will focus on the use of IP-RP-HPLC, a particularly powerful and convenient form of IP-RPC. It is to be understood that this is not intended to limit the scope of the invention, and that generally the methods described can be performed without the use of HPLC, although this will in some cases lead to less than optimal results. IP-RPC is a form of chromatography characterized by the use of a reversed phase (i.e., hydrophobic) stationary phase and a mobile phase that includes an alkylated cation (e.g., triethylammonium) that is believed to form a bridging interaction between the negatively charged polynucleotide and non-polar stationary phase. The alkylated cation-mediated interaction of polynucleotide and stationary phase can be modulated by the polarity of the mobile phase, conveniently adjusted by means of a solvent that is less polar than water, e.g., acetonitrile. In general, a polynucleotide such as RNA is retained by the separation medium in the presence of counterion agent, and can be eluted by increasing the concentration of a non-polar solvent. Elution can be accomplished in the presence or absence of counterion agent. Performance is enhanced by the use of a non-porous separation medium, as described in U.S. patent application Ser. No. 5,585,236. A superior form of IP-RP-HPLC, termed Matched Ion Polynucleotide Chromatography (MIPC), is described in U.S. Pat. Nos. 5,585,236, 6,066,258 and 6,056,877 and PCT Publication Nos. WO98/48913, WO98/48914, WO/98/56797, W098/56798, incorporated herein by reference in their entirety. MIPC is characterized by the use of solvents and chromatographic surfaces that are substantially free of multivalent cation contamination that can interfere with polynucleotide separation. In the practice of the instant invention, a preferred system for performing MIPC separations is that provided by Transgenomic, Inc. under the trademark WAVE®.

Separation by RP-IP-HPLC, including MIPC, occurs at the non-polar surface of a separation medium. In one embodiment, the non-polar surfaces comprise the surfaces of polymeric beads. In an alternative embodiment, the surfaces comprise the surfaces of interstitial spaces in a molded polymeric monolith, described in more detail infra. For purposes of simplifying the description of the invention and not by way of limitation, the separation of polynucleotides using nonporous beads, and the preparation of such beads, will be primarily described herein, it being understood that other separation surfaces, such as the interstitial surfaces of polymeric monoliths, are intended to be included within the scope of this invention.

In general, in order to be suitable for use in IP-RP-HPLC a separation medium should have a surface that is either intrinsically non-polar or bonded with a material that forms a surface having sufficient non-polarity to interact with a counterion agent.

In one aspect of the invention, IP-RP-HPLC detection is accomplished using a column filled with nonporous polymeric beads having an average diameter of about 0.5–100 microns; preferably, 1–10 microns; more preferably, 1–5 microns. Beads having an average diameter of 1.0–3.0 microns are most preferred.

In a preferred embodiment of the invention, the chromatographic separation medium comprises nonporous beads, i.e., beads having a pore size that essentially excludes the polynucleotides being separated from entering the bead, although porous beads can also be used. As used herein, the term "nonporous" is defined to denote a bead that has surface pores having a diameter that is sufficiently small so as to effectively exclude the smallest DNA fragment in the separation in the solvent medium used therein. Included in this definition are polymer beads having these specified maximum size restrictions in their natural state or which have been treated to reduce their pore size to meet the maximum effective pore size required.

The surface conformations of nonporous beads of the present invention can include depressions and shallow pit-like structures that do not interfere with the separation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Without intending to be bound by any particular theory, it is believed that pores having dimensions that allow movement of the polynucleotide into the interconnected pore structure and into the bead impair the resolution of separations or result in separations that have very long retention times.

Non-porous polymeric beads useful in the practice of the present invention can be prepared by a two-step process in which small seed beads are initially produced by emulsion polymerization of suitable polymerizable monomers. The emulsion polymerization procedure is a modification of the procedure of Goodwin, et al. (*Colloid & Polymer Sci.*, 252:464–471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably in the range of about 100:1 to about 500:1, more preferably about 200:1 in order to ensure a degree of polymerization of at least 200. Beads having this degree of polymerization are sufficiently pressure-stable to be used in HPLC applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

For use in the present invention, packing material disclosed by U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation can be achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term alkyl as used herein in reference to the beads useful in the practice of the present invention is defined to include alkyl and alkyl substituted aryl groups, having from 1 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which are considered to be non-polar, reverse phase functional groups.

Non-limiting examples of base polymers suitable for use in producing such polymer beads include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly (styrene-divinylbenzene) and poly(ethylvinylbenzene-divinylbenzene). Methods for making beads from these polymers are conventional and well known in the art (for example, see U.S. Pat. No. 4,906,378). The physical properties of the surface and near-surface areas of the beads are the primary determinant of chromatographic efficiency. The polymer, whether derivatized or not, should provide a nonporous, non-reactive, and non-polar surface for the MIPC separation. In a particularly preferred embodiment of the invention, the separation medium consists of octadecyl modified, nonporous alkylated poly(styrene-divinylbenzene) beads. Separation columns employing these particularly preferred beads, referred to as DNASep® columns, are commercially available from Transgenomic, Inc.

A separation bead used in the invention can comprise a nonporous particle which has non-polar molecules or a non-polar polymer attached to or coated on its surface. In general, such beads comprise nonporous particles which have been coated with a polymer or which have substantially all surface substrate groups reacted with a non-polar hydrocarbon or substituted hydrocarbon group, and any remaining surface substrate groups endcapped with a tri(lower alkyl) chlorosilane or tetra(lower alkyl)dichlorodisilazane as described in U.S Pat. No. 6,056,877.

The nonporous particle is preferably an inorganic particle, but can be a nonporous organic particle. The nonporous particle can be, for example, silica, silica carbide, silica nitrite, titanium oxide, aluminum oxide, zirconium oxide, carbon, insoluble polysaccharides such as cellulose, or diatomaceous earth, or any of these materials which have been modified to be nonporous. Examples of carbon particles include diamond and graphite which have been treated to remove any interfering contaminants. The preferred particles are essentially non-deformable and can withstand high pressures. The nonporous particle is prepared by known procedures. The preferred particle size is about 0.5–100 microns; preferably, 1–10 microns; more preferably, 1–5 microns. Beads having an average diameter of 1.0–3.0 microns are most preferred.

Because the chemistry of preparing conventional silica-based reverse phase HPLC materials is well-known, most of the description of non-porous beads suitable for use in the instant invention is presented in reference to silica. It is to be understood, however, that other nonporous particles, such as those listed above, can be modified in the same manner and substituted for silica. For a description of the general chemistry of silica, see Poole, Colin F. and Salwa K. Poole, *Chromatography Today*, Elsevier:New York (1991), pp. 313–342 and Snyder, R. L. and J. J. Kirkland, *Introduction to Modern Liquid Chromatography*, 2$^{nd}$ ed., John Wiley & Sons, Inc.:New York (1979), pp. 272–278, the disclosures of which are hereby incorporated herein by reference in their entireties.

The nonporous beads of the invention are characterized by having minimum exposed silanol groups after reaction with the coating or silating reagents. Minimum silanol groups are needed to reduce the interaction of the DNA with the substrate and also to improve the stability of the material in a high pH and aqueous environment. Silanol groups can be harmful because they can repel the negative charge of the DNA molecule, preventing or limiting the interaction of the DNA with the stationary phase of the column. Another possible mechanism of interaction is that the silanol can act as ion exchange sites, taking up metals such as iron (III) or chromium (III). Iron (III) or other metals which are trapped on the column can distort the DNA peaks or even prevent DNA from being eluted from the column.

Silanol groups can be hydrolyzed by the aqueous-based mobile phase. Hydrolysis will increase the polarity and reactivity of the stationary phase by exposing more silanol sites, or by exposing metals that can be present in the silica core. Hydrolysis will be more prevalent with increased underivatized silanol groups. The effect of silanol groups on the DNA separation depends on which mechanism of interference is most prevalent. For example, iron (III) can become attached to the exposed silanol sites, depending on whether the iron (III) is present in the eluent, instrument or sample.

The effect of metals can only occur if metals are already present within the system or reagents. Metals present within the system or reagents can get trapped by ion exchange sites on the silica. However, if no metals are present within the system or reagents, then the silanol groups themselves can cause interference with DNA separations. Hydrolysis of the exposed silanol sites by the aqueous environment can expose metals that might be present in the silica core.

Fully hydrolyzed silica contains a concentration of about 8 μmoles of silanol groups per square meter of surface. At best, because of steric considerations, a maximum of about 4.5 μmoles of silanol groups per square meter can be reacted, the remainder of the silanol being sterically shielded by the reacted groups. Minimum silanol groups is defined as reaching the theoretical limit of or having sufficient shield to prevent silanol groups from interfering with the separation.

Numerous methods exist for forming nonporous silica core particles. For example, sodium silicate solution poured into methanol will produce a suspension of finely divided spherical particles of sodium silicate. These particles are neutralized by reaction with acid. In this way, globular particles of silica gel are obtained having a diameter of about 1–2 microns. Silica can be precipitated from organic liquids or from a vapor. At high temperature (about 2000° C.), silica is vaporized, and the vapors can be condensed to form finely divided silica either by a reduction in temperature or by using an oxidizing gas. The synthesis and properties of silica are described by R. K. Iler in *The Chemistry of Silica, Solubility, Polymerization, Colloid and Surface Properties, and Biochemistry*, John Wiley & Sons:New York (1979).

W. Stöber et al. described controlled growth of monodisperse silica spheres in the micron size range in *J. Colloid and Interface Sci.*, 26:62–69 (1968). Stöber et al. describe a system of chemical reactions which permit the controlled growth of spherical silica particles of uniform size by means of hydrolysis of alkyl silicates and subsequent condensation of silicic acid in alcoholic solutions. Ammonia is used as a morphological catalyst. Particle sizes obtained in suspension range from less than 0.05 μm to 2 μm in diameter.

To prepare a nonporous bead, the nonporous particle can be coated with a polymer or reacted and endcapped so that substantially all surface substrate groups of the nonporous particle are blocked with a non-polar hydrocarbon or substituted hydrocarbon group. This can be accomplished by any of several methods described in U.S. Pat. No. 6,056,877. Care should be taken during the preparation of the beads to ensure that the surface of the beads has minimum silanol or metal oxide exposure and that the surface remains nonporous. Nonporous silica core beads can be obtained from Micra Scientific (Northbrook, Ill.) and from Chemie Uetikkon (Lausanne, Switzerland).

In another embodiment of the present invention, the IP-RP-HPLC separation medium can be in the form of a polymeric monolith, e.g., a rod-like monolithic column. A monolith is a polymer separation media, formed inside a column, having a unitary structure with through pores or interstitial spaces that allow eluting solvent and analyte to pass through and which provide the non-polar separation surface, as described in U.S. Pat. No. 6,066,258 and U.S. patent application Ser. No. 09/562,069. The interstitial separation surfaces can be porous, but are preferably nonporous. The separation principles involved parallel those encountered with bead-packed columns. As with beads, pores traversing the monolith must be compatible with and permeable to DNA. In a preferred embodiment, the rod is substantially free of contamination capable of reacting with DNA and interfering with its separation, e.g., multivalent cations.

A molded polymeric monolith rod that can be used in practicing the present invention can be prepared, for example, by bulk free radical polymerization within the confines of a chromatographic column. The base polymer of the rod can be produced from a variety of polymerizable monomers. For example, the monolithic rod can be made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly (glycidyl methacrylate-co-ethylene dimethacrylate), poly (styrene-divinylbenzene) and poly(ethylvinylbenzene-divinylbenzene. The rod can be unsubsituted or substituted with a substituent such as a hydrocarbon alkyl or an aryl group. The alkyl group optionally has 1 to 1,000,000 carbons inclusive in a straight or branched chain, and includes straight chained, branch chained, cyclic, saturated, unsaturated nonionic functional groups of various types including aldehyde, ketone, ester, ether, alkyl groups, and the like, and the aryl groups includes as monocyclic, bicyclic, and tricyclic aromatic hydrocarbon groups including phenyl, naphthyl, and the like. In a preferred embodiment, the alkyl group has 1–24 carbons. In a more preferred embodiment, the alkyl group has 1–8 carbons. The substitution can also contain hydroxy, cyano, nitro groups, or the like which are considered to be non-polar, reverse phase functional groups. Methods for hydrocarbon substitution are conventional and well-known in the art and are not an aspect of this invention. The preparation of polymeric monoliths is by conventional methods well known in the art as described in the following references: Wang et al.(1994) *J. Chromatog. A* 699:230; Petro et al. (1996) *Anal. Chem.* 68:315 and U.S. Pat. Nos. 5,334,310; 5,453,185 and 5,522,994. Monolith or rod columns are commercially available form Merck & Co (Darmstadt, Germany).

The separation medium can take the form of a continuous monolithic silica gel. A molded monolith can be prepared by polymerization within the confines of a chromatographic column (e.g., to form a rod) or other containment system. A monolith is preferably obtained by the hydrolysis and polycondensation of alkoxysilanes. A preferred monolith is derivatized in order to produce non-polar interstitial surfaces. Chemical modification of silica monoliths with ocatdecyl, methyl or other ligands can be carried out. An example of a preferred derivatized monolith is one which is polyfunctionally derivatized with octadecylsilyl groups. The preparation of derivatized silica monoliths can be accomplished using conventional methods well known in the art as described in the following references which are hereby incorporated in their entirety herein: U.S Pat. No. 6,056,877, Nakanishi, et al., *J. Sol-Gel Sci. Technol.* 8:547 (1997); Nakanishi, et al., *Bull, Chem. Soc. Jpn.* 67:1327 (1994); Cabrera, et al., *Trends Analytical Chem.* 17:50 (1998); Jinno, et al., *Chromatographia* 27:288 (1989).

MIPC is characterized by the use of a separation medium having low amounts of metal contaminants or other contaminants that can bind DNA. Preferred beads and monoliths have been produced under conditions where precautions have been taken to substantially eliminate any multivalent cation contaminants (e.g. Fe(III), Cr(III), or colloidal metal contaminants), including a decontamination treatment, e.g., an acid wash treatment. Only very pure, non-metal containing materials should be used in the production of the beads in order to minimize the metal content of the resulting beads.

In addition to the separation medium being substantially metal-free, to achieve optimum peak separation the separation column and all process solutions held within the column or flowing through the column are preferably substantially free of multivalent cation contaminants (e.g. Fe(III), Cr(III), and colloidal metal contaminants). As described in U.S. Pat. Nos. 5,772,889, 5,997,742 and 6,017,457, this can be achieved by supplying and feeding solutions that enter the separation column with components that have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer. Metals found in stainless steel, for example, do not harm the separation, unless they are in an oxidized or colloidal partially oxidized state. For example, 316 stainless steel frits are acceptable in column hardware, but surface oxidized stainless steel frits harm the DNA separation.

For additional protection, multivalent cations in mobile phase solutions and sample solutions entering the column can be removed by contacting these solutions with multivalent cation capture resin before the solutions enter the column to protect the separation medium from multivalent cation contamination. The multivalent capture resin is preferably cation exchange resin and/or chelating resin.

Trace levels of multivalent cations anywhere in the solvent flow path can cause a significant deterioration in the resolution of the separation after multiple uses of an IP-RP-HPLC column. This can result in increased cost caused by the need to purchase replacement columns and increased downtime. Therefore, effective measures are preferably taken to prevent multivalent metal cation contamination of the separation system components, including separation media and mobile phase contacting. These measures include, but are not limited to, washing protocols to remove traces of multivalent cations from the separation media and installation of guard cartridges containing cation capture resins, in line between the mobile phase reservoir and the MIPC column. These, and similar measures, taken to prevent system contamination with multivalent cations have resulted in extended column life and reduced analysis downtime.

There are two places where multivalent-cation-binding agents, e.g., chelators, are used in MIPC separations. In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In another embodiment, the multivalent cation-binding agent can be added to the mobile phase. The binding functional group is incorporated into an organic chemical structure. The preferred multivalent cation-binding agent fulfills three requirements. First, it is soluble in the mobile phase. Second, the complex with the metal is soluble in the mobile phase. Multivalent cation-binding agents such as EDTA fulfill this requirement because both the chelator and the multivalent cation-binding agent-metal complex contain charges, which makes them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation-binding agent can be easily removed from the column by washing with water, organic solvent or mobile phase. Third, the binding agent must not interfere with the chromatographic process.

The multivalent cation-binding agent can be a coordination compound. Examples of preferred coordination compounds include water soluble chelating agents and crown ethers. Non-limiting examples of multivalent cation-binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis*, Robert E. Krieger Publishing Co. (1964). In the present invention, a preferred multivalent cation-binding agent is EDTA.

To achieve high-resolution chromatographic separations of polynucleotides, it is generally necessary to tightly pack the chromatographic column with the solid phase polymer beads. Any known method of packing the column with a column packing material can be used in the present invention to obtain adequate high-resolution separations. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonication is typically used to improve packing density.

For example, to pack a 50×4.6 mm I.D. column, 2.0 grams of beads can be suspended in 10 mL of methanol with the aid of sonication. The suspension is then packed into the column using 50 mL of methanol at 8,000 psi of pressure. This improves the density of the packed bed.

There are several types of counterions suitable for use with IP-RP-HPLC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

Without intending to be bound by any particular theory, it is believed the alkyl group functions by imparting a nonpolar character to the DNA through an ion pairing process so that the DNA can interact with the nonpolar surface of the separation media. The requirements for the degree of nonpolarity of the counterion-DNA pair depends on the polarity of the separation media, the solvent conditions required for separation, the particular size and type of fragment being separated. For example, if the polarity of the separation media is increased, then the polarity of the counterion agent may have to be adjusted to match the polarity of the surface and increase interaction of the counterion-DNA pair. In general, as the size and hydrophobicity of the alkyl group is increased, the separation is less influenced by DNA sequence and base composition, but rather is based predominately on DNA sequence length.

In some cases, it may be desired to increase the range of concentration of organic solvent used to perform the separation. For example, increasing the alkyl chain length on the counterion agent will increase the nonpolarity of the counterion-DNA pair resulting in the need to either increase the concentration of the mobile phase organic solvent, or increase the strength of the organic solvent type, e.g., acetonitrile is about two times more effective than methanol for eluting DNA. There is a positive correlation between concentration of the organic solvent required to elute a fragment from the column and the length of the fragment. However, at high organic solvent concentrations, the polynucleotide can precipitate. To avoid precipitation, a more non-polar organic solvent and/or a smaller counterion alkyl group can be used. The alkyl group on the counterion agent can also be substituted with halides, nitro groups, or the like to modulate polarity.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkylammonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, dimethydiethylammonium acetate, triethylammonium acetate, tripropylammonium acetate, tributylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography*, 2nd Ed., Dr. Alfred Hüthig Verlag Heidelberg (1987). In a particularly preferred embodiment of the invention the counterion tetrabutylammonium bromide (TBAB) is preferred, although other quaternary ammonium reagents such as tetrapropyl or tetrabutyl ammonium salts can be used. Alternatively, a trialkylammonium salt, e.g., triethylammonium acetate (TEAA) can be used.

The pH of the mobile phase is preferably within the range of about pH 5 to about pH 9, and optimally within the range of about pH 6 to about pH 7.5.

To achieve optimum peak resolution during the separation of DNA by IP-RP-HPLC, the method is preferably performed at a temperature within the range of 20° C. to 90° C.; more preferably, 30° C. to 80° C.; most preferably, 50° C. to 75° C. The flow rate is selected to yield a back pressure not exceeding 5000 psi. In general, separation of single-stranded fragments should be performed at higher temperatures. In a preferred embodiment of the invention, the separation is achieved at a temperature at which the amplified extension product is denatured. The temperature required to achieve denaturation will vary, depending upon the nature of the column, the mobile phase and counterion agent used, and the melting properties of the DNA being separated. In a particularly preferred embodiment of the invention, where the separation medium is octadecyl modified, nonporous alkylated poly(styrene-divinylbenzene) beads, the aqueous mobile phase contains acetonitrile and TBAB is used as a counterion, the column temperature is preferably greater than 50° C., more preferably between about 50° C. and 80° C., and most preferably about 70° C.

The temperature at which the separation is performed affects the choice of organic solvents used in the separation, and vice versa. The solvent affects the temperature at which a double stranded DNA will melt to form two single strands or a partially melted complex of single and double stranded DNA, i.e., some solvents will stabilize a DNA duplex better than others. Furthermore, the polarity of a solvent affects the distribution of the DNA between the mobile phase and the stationary phase.

An organic solvent that is water soluble is preferably used, e.g., an alcohol, nitrile, dimethylformamide (DMF), tetrahydrofuran (THF), ester, or ether. Water soluble solvents are defined as those that exist as a single phase with aqueous systems under all conditions of operation of the present invention. For example, acetonitrile and 1-propanol have polarity and solubility properties that are particularly suited for use in the present invention. However, methanol can be a good alternative that reduces cost and toxicity concerns. Solvents that are particularly preferred for use in the method of this invention include methanol, ethanol, 2-propanol, 1-propanol, tetrahydrofuran (THF), and acetonitrile, with acetonitrile being most preferred overall.

In performing IP-RP-HPLC and MIPC, even trace levels of multivalent cations anywhere in the solvent flow path can cause a significant deterioration in the resolution of the separation after multiple uses of a column. This can result in increased cost caused by the need to purchase replacement columns and increased downtime. Therefore, effective measures are preferably taken to prevent multivalent metal cation contamination of the separation system components, including separation media and mobile phase contacting. These measures include, but are not limited to, washing protocols to remove traces of multivalent cations from the separation media and installation of guard cartridges containing cation capture resins, in line between the mobile phase reservoir and the column. These, and similar measures, taken to prevent system contamination with multivalent cations have resulted in extended column life and reduced analysis downtime.

In some instances, in order to optimize column life and maintain effective separation performance, it will be desirable to periodically run an aqueous solution of multivalent cation-binding agent through the column, e.g., after about 500 uses or when the performance starts to degrade. Examples of suitable cation-binding agents are as described hereinabove.

The concentration of a solution of the cation-binding agent can be between 0.01M and 1M. In a preferred embodiment, the column washing solution contains EDTA at a concentration of about 0.03 to 0.1M.

In another embodiment, the solution contains an organic solvent selected from the group consisting of acetonitrile, ethanol, methanol, 2-propanol, and ethyl acetate. A preferred solution contains at least 2% organic solvent to prevent microbial growth. In a most preferred embodiment a solution containing 25% acetonitrile is used to wash a column. The multivalent cation-binding solution can contain a counterion agent as described hereinabove.

In one embodiment of a column washing procedure, the separation column is washed with the multivalent cation-binding solution at an elevated temperature in the range of 50° C. to 80° C. In a preferred embodiment the column is washed with a solution containing EDTA, TEAA, and acetonitrile, in the 70° C. to 80° C. temperature range. In a specific embodiment, the solution contains 0.032 M EDTA, 0.1M TEAA, and 25% acetonitrile.

Column washing can range from 30 seconds to one hour. In a preferred procedure, the column is washed with multivalent cation-binding agent for 30 to 60 minutes at a flow rate preferably in the range of about 0.05 to 1.0 mL/min.

Other treatments for washing a column can also be used alone or in combination with those indicated hereinabove. These include: use of high pH washing solutions (e.g., pH 10–12), use of denaturants such as urea or formamide, and reverse flushing the column with washing solution.

MIPC separation efficiency can be preserved by storing the column separation media in the presence of a solution of multivalent cation-binding agent. The solution of binding agent may also contain a counterion agent. Any of the multivalent cation-binding agents, counterion agents, and solvents described hereinabove are suitable for the purpose of storing a MIPC column. In a preferred embodiment, a column packed with MIPC separation media is stored in an organic solvent containing a multivalent cation-binding agent and a counterion agent. An example of this preferred embodiment is 0.032 M EDTA and 0.1M TEAA in 25% aqueous acetonitrile. In preparation for storage, a solution of multivalent cation-binding agent, as described above, is passed through the column for about 30 minutes. The column is then disconnected from the HPLC apparatus and the column ends are capped with commercially available threaded end caps made of material which does not release multivalent cations. Such end caps can be made of coated stainless steel, titanium, organic polymer or any combination thereof.

High pressure pumps are used for pumping mobile phase in the systems described in U.S. Pat. No. 5,585,236 to Bonn and in U.S. Pat. No. 5,772,889 to Gjerde. It will be appreciated that other methods are known for driving mobile phase through separation media and can be used in carrying out the analysis described in the present invention. A non-limiting example of such an alternative method includes "capillary electrochromatography" (CEC) in which an electric field is applied across capillary columns packed with microparticles and the resulting electroosmotic flow acts as a pump for chromatography. Electroosmosis is the flow of liquid, in contact with a solid surface, under the influence of a tangentially applied electric field. The technique combines the advantages of the high efficiency obtained with capillary electrophoretic separations, such as capillary zone electrophoresis, and the general applicability of HPLC. CEC has the capability to drive the mobile phase through columns packed with chromatographic particles, especially small particles, when using electroosmotic flow. High efficiencies can be obtained as a result of the plug-like flow profile. In the use of CEC in the present invention, solvent gradients are used and rapid separations can be obtained using high electric fields. The following references describing CEC are each incorporated in their entirety herein: Dadoo, et al, *LC-GC* 15:630 (1997); Jorgenson, et al., *J. Chromatog.* 218:209 (1981); Pretorius, et al., *J. Chromatog.* 99:23 (1974); and the following U.S. Pat. Nos. to Dadoo U.S. Pat. No. 5,378,334 (1995), U.S. Pat. No. 5,342,492 (1994), and U.S. Pat. No. 5,310,463 (1994). In the operation of this aspect of the present invention, the capillaries are packed, either electrokinetically or using a pump, with the separation beads described in the present specification. In another embodiment, a polymeric rod is prepared by bulk free radical polymerization within the confines of a capillary column. Capillaries are preferably formed from fused silica tubing or etched into a block. The packed capillary (e.g., a 150-$\mu$m i.d. with a 20-cm packed length and a window located immediately before the outlet frit) is fitted with frits at the inlet and outlet ends. An electric field, e.g., 2800V/cm, is applied. Detection can be by uv absorbance or by fluorescence. A gradient of organic solvent, e.g., acetonitrile, is applied in a mobile phase containing counterion agent (e.g. 0.1 M TEAA) to elute the polynucleotides. The column temperature is maintained by conventional temperature control means. In the preferred embodiment, all of the precautions for minimizing trace metal contaminants as described hereinabove are employed in using CEC.

IP-RP-HPLC has been applied to DNA for purposes such as sizing, purification, quantitative reverse transcription-polymerase chain reaction (RT-PCR), and mutation detection. See, for example, Huber, C. G., Oefner, P. J., and Bonn, G. K. (1995) *Anal. Chem.* 67, 578–585; Hecker, K. H., Turpie, B., and Kuklin, A. (1999) *Biotechniques.* 26, 216–8; Hayward-Lester, A., Oefner, P. J., and Doris, P. A. (1996) *Biotechniques* 20, 250–7; Hayward-Lester, A., Oefner, P. J., Sabatini, S., Kainer, D. B., Hinojos, C. A., and Doris, P. A. (1998) 26, 2511–18; Kuklin, A., Munson, K., Gjerde, D., Haefele, R., and Taylor, P. (1998) *Genet Test.* 1,201–6; O'Donovan, M. C. et al. (1998) *Genomics* 52, 44–9; Kuklin, A., Davis, A. P., Hecker, K. H., Gjerde, D. T., and Taylor, P. D. (1999) *Mol Cell Probes* 13, 239–42; and Wagner, T. et al. (1999) *Genomics* 62, 369–76. Reported RNA applications of IP-RP-HPLC RNA resolution, integrity determination, quantification, and purification, as reported, for example, by Azarani, A. Haefele, R., and Hecker, K. H. (2000) *Miami Nature Biotechnology Short Reports* 11, 29; Georgopoulos, D. E., and Leibowitz, M. J. (1999) *J. Chromatography* 868, 109–14; Azarani, A., and Hecker, K. H. RNA analysis by ion-pair reversed-phase high performance liquid chromatography. *Nucleic Acids Research* (2001) (in press).

In one embodiment of the invention, IP-RPC separation can be accomplished by means of a batch process. In this embodiment, a relatively polar sample solution containing the mRNA pool, including a counterion agent, are mixed in bulk with separation beads in a container, whereby mRNA binds to the beads. Preferably, all of the mRNA-counterion aggregates will bind nonspecifically to the beads under the initial loading conditions. To release mRNA from the beads, the beads are brought into contact with an elution solution with a sufficient concentration of organic solvent to effect elution of the desired polynucleotides. Elution conditions for desired relative size ranges of mRNA molecules can often be predetermined, e.g. by determining the elution profile of a standard mRNA mixture at various concentrations of organic solvent. This calibration procedure can be conducted on a small scale and applied to a large-scale process. This type of batch process is described in more detail in U.S. patent application Ser. No. 09/391,963.

In performing IP-RPC in a batch mode, a plurality of mRNA molecules is bound to the separation mdium, after which a wash solution is applied in a first release step in which the organic solvent is applied at a concentration which will release non-targeted mRNA molecules. The beads are then separated from the solvent, e.g. by centrifugation or by filtration. An elution solution is then applied to the beads in a second release step in which the elution solution contains an incrementally elevated concentration of organic solvent, which selectively releases target mRNA molecule, e.g., mRNA molecules of a desired relative size range. Optionally, the process can be repeated with the application of elution solutions containing increasing concentrations of organic solvent in order to successively release mRNA fractions characterized by increasing affinity for the separation medium; generally affinity is based at least in part on mRNA size. Each fraction can be recovered, e.g. by collecting the elution solution at each concentration of organic solvent. It is possible to have multiple wash steps at a single concentration of organic solvent to ensure complete removal of targeted molecules.

In another example of a batch process of the present invention, the separation is performed using a column, e.g. an open column under gravity flow conditions or a low pressure column equipped with a peristaltic pump. The separation medium comprises beads having a diameter large enough to permit flow of elution solution without requiring high pressure pumps. Preferred beads have a diameter of about 10 to 1000 microns and can be made from various materials as described hereinabove. The dimensions of the column can range from about 10 cm to 1 m in length, and 1 to 100 cm in diameter, for example. In operation, the column is first conditioned using a polar solvent. Typically an RNA-counterion mixture is applied to the column in a convenient volume such as from 1 to 50 mL. For dilute samples having a large volume, the sample can be applied continuously, or in stages, to "load" the column. Preferably, all of the RNA-counterion aggregate will bind to the separation medium under the initial conditions in which the loading solution has low concentration of organic solvent. To release targeted RNA molecules from the separation beads, the beads are brought into contact with an elution solution having a sufficient concentration of organic solvent. Elution conditions for specific RNA molecules, or molecules of a desired relative size range, can be pre-determined, e.g. by determining the elution profile of a standard mRNA mixture at various concentrations of solvent. This calibration procedure can be conducted on a small scale and applied to a large-scale process. Specific solvent compositions can be adjusted to elute a targeted RNA in analogy to the bulk equilibria process as described hereinabove. After the sample mixture is bound to the separation medium in the column, a wash solution can be applied in a first release step in which the organic solvent is present at a concentration which will release non-RNA contaminating species (e.g. macromolecules such as proteins, DNA molecules or carbohydrates) and/or non-targeted RNA molecules having less affinity for the separation medium than targeted RNA molecules; an elution solution is then applied in a second release step in which the organic solvent is present at an elevated concentration, e.g. an incrementally elevated concentration, which selectively releases the targeted RNA molecules, e.g., fractions of mRNA molecules enriched for mRNA molecules of a desired size range relative to the plurality of mRNA molecules applied to the column. Optionally, organic solvents can be applied in a gradient of increasing concentration, e.g. a step-gradient or continuous gradient, in order to progressively release RNA molecules having increasing affinity for the separation medium. Each fraction is recovered, for example, by collecting the elution solution at each concentration of organic solvent. For each fraction, the separation process can be repeated, if necessary, e.g. by application to another column.

In another embodiment of the invention, the separation medium can be retained in a web or pad. An example is a web of inert fiber matrix with hydrophobic separation medium, such as the beads as described hereinabove, enmeshed in the matrix. The web of the present invention is a composite article comprising separation medium which has been incorporated into a fabric or membrane. The term "incorporated into a fabric membrane" means that the separation medium is encapsulated by or trapped within a fabric or membrane, is stabilized within a fabric or membrane or is covalently attached to a fabric or membrane such that the separation medium does not exist as free flowable particulate bulk material and is not separable from the web under liquid chromatography conditions.

In another embodiment of the invention, the separation medium is incorporated into a web, which may be woven or non-woven. The spaces between fibers of the web should be small enough to prevent separation medium material from passing through the web. The density of non-woven fibers and the density of warp and weft fibers of the web can be routinely adjusted to provide the desired density and porosity.

The web fibers can be made of any suitable material so long as the material is porous. Suitable materials are described in U.S. Pat. No. 5,338,448. Generally, the fibers will be made of a porous synthetic or natural polymeric material, e.g. polytetrafluoroethylene, cellulose, polyvinyl chloride, nylon, etc. The RNA in the sample preferably binds only to the separation medium and the binding is not detrimentally affected by the fiber matrix material. When the separation medium consists of polymeric beads, the ratio of beads to fiber matrix material can be in the range of 19:1 to 4:1 by weight, for example.

In one embodiment, the web is mounted on a support and the sample is applied and eluted in a manner analogous to the open column process as described hereinabove. The web material can be packed into a column. An advantage of using a web material is that it provides flexibility in how thin a column bed can be made, e.g. the web can be formed as a disk. Also, several uniform beds can be made at once. Multiple webs can be supported in a row or adapted to a matrix well format, e.g. a multi-well plate. The web can be used in analogy to the bulk equilibria process or column as described hereinabove with a binding step followed by release steps.

An example of a suitable fibril matrix is polytetrafluoroethylene (PTFE) as described in U.S. Pat. No. 4,906,378 to Hagen. The ratio of beads to PTFE fibril matrix can be in the range of 19:1 to 4:1 by weight, for example.

Figure 3A:
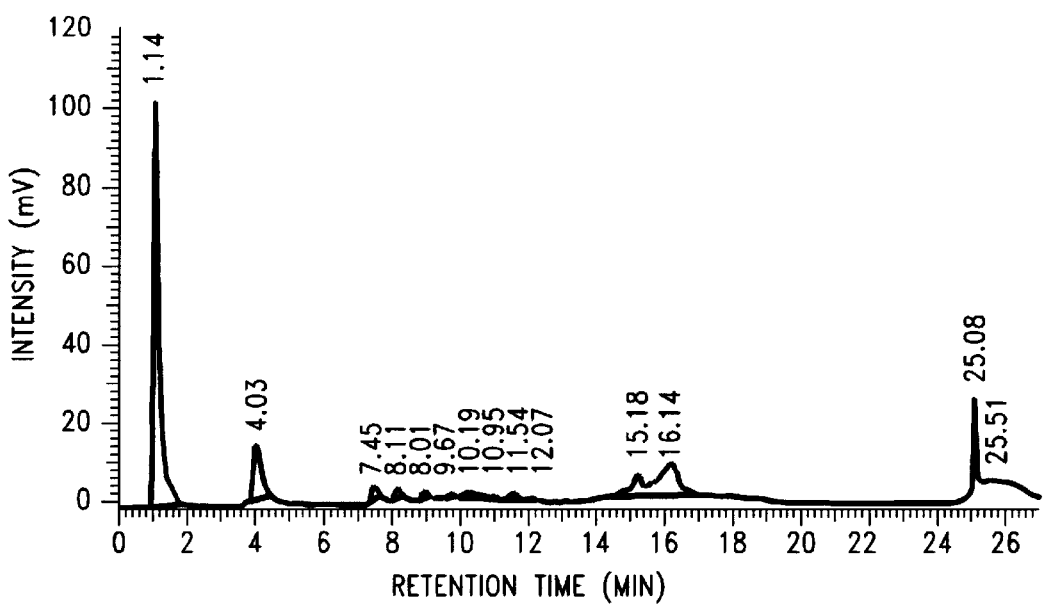
FIGS. 3A, 3B, and 3C are a chromatograms obtained for fractionation of an RNA ladder by IP-RP-HPLC on a silica based column at 50° C., 65° C., and 75° C., respectively.
Figure 3B:
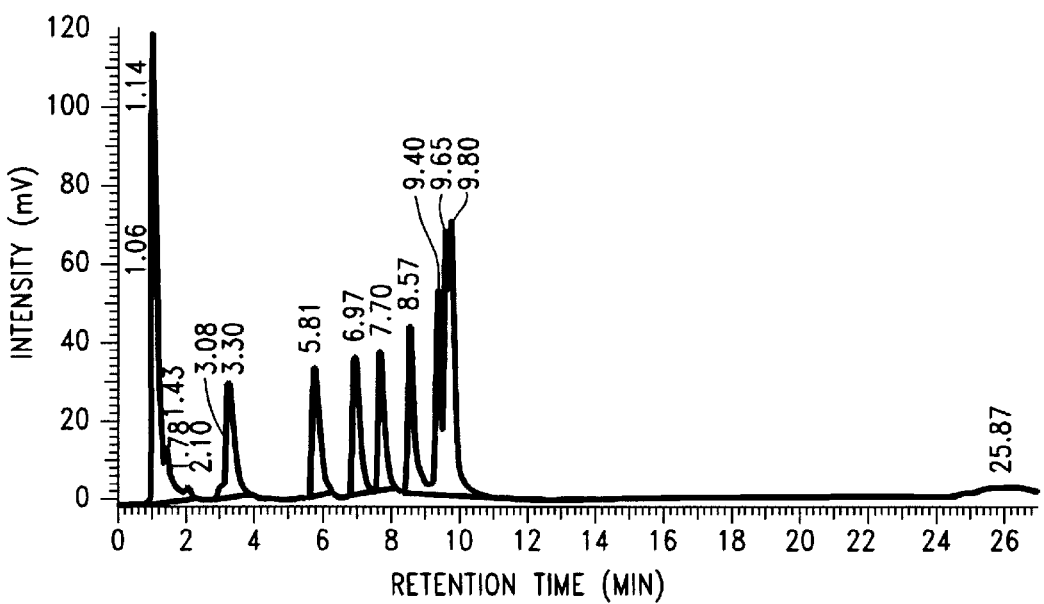
Figure 3C:
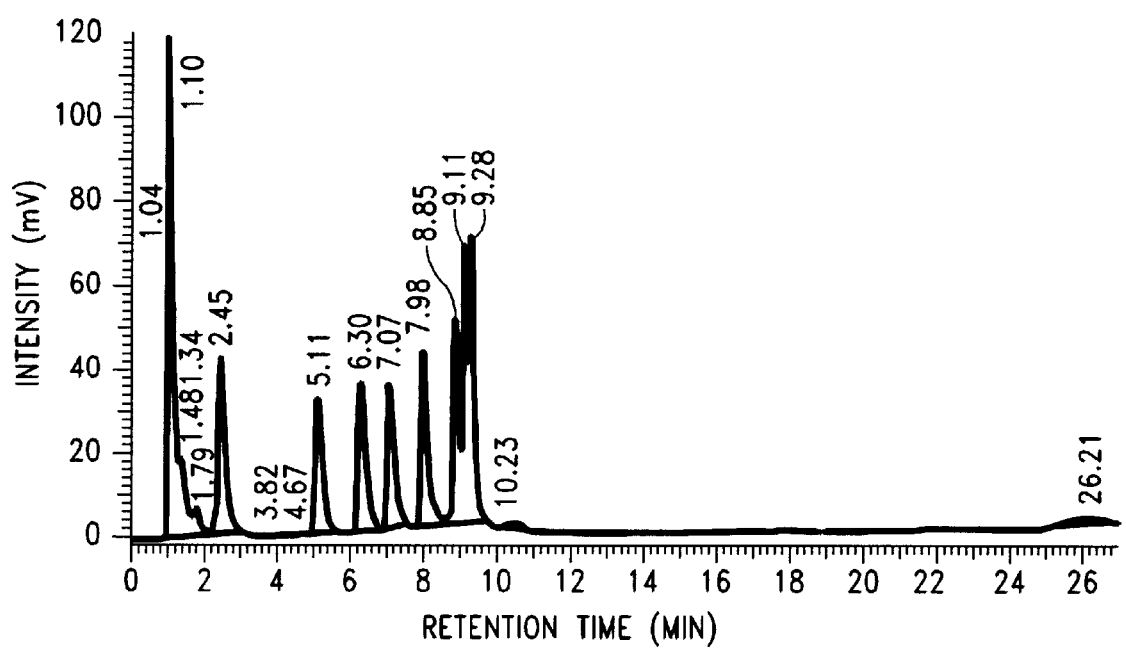

In another embodiment of the invention, IP-RPC separation is accomplished using a spin column. FIG. 3 is a cross-sectional view of a spin column separation device suitable for such a use. In this embodiment a standard laboratory centrifuge is used to rapidly pass liquids through the separation media. The system uses a standard cylindrical centrifuge vial or eluant container 142 into which a separator tube or cylinder 144 is inserted. The separator cylinder can have a cylindrical body 146, open at top end 148 and bottom end 150, and sized to fit within the vial 142. The upper end 148 has an outwardly extending upper flange 152 which is sized to rest on the upper rim 154 of the cylindrical vial 142. The lower end 150 has an inwardly extending lower flange 156 which is sized to support the separation unit 158.

The separation unit comprises a porous support disk 160 which rests on flange 156, an optional outer cylinder 162 within which the separation media 164 is positioned. The separation unit can also comprise an optional upper porous disk 166 to prevent disruption of the separation media and an optional ring 168. The optional ring 168 preferably has a slightly elastic or yielding composition and an outer diameter which is sized to establish a frictional engagement with the inner wall of cylinder 146. The ring 168, when pressed against the disk 166, holds the disk in place during use of the column.

In general, mRNA separations can be achieved by applying the following sequence of non-limiting steps.

1. A solution containing the mRNA molecules of interest is diluted in a loading solution containing an appropriate counterion agent and no organic solvent, or a concentration of organic solvent below that which is required to cause elution of mRNAs of a desired relative size range.

2. The diluted mixture is placed into chamber 170 and the spin column is placed in a standard laboratory centrifuge and spun until all of the free liquid has passed into the chamber 172. The inner cylinder 144 is removed from the vial, and the contents of chamber 172 are discarded (or saved if so desired). mRNA molecules to be separated bind to the separation medium in this step.

3. If so desired, a wash solution containing counterion and an organic solvent is added to chamber 170. The organic solvent concentration is calculated to be the amount which will remove non-targeted molecules that have less affinity for the separation medium than the targeted fraction of mRNA molecules. If desired, the appropriate concentration of organic solvent can be pre-determined as described supra.

4. If a wash step is used, the separation device is spun in a centrifuge until all of the free wash solution has passed into the chamber 172. The inner cylinder 144 is removed from the vial, and the contents of chamber 172 are removed. This step removes from the separation medium contaminants and other non-targeted molecules that have less affinity for the separation medium than the targeted fraction.

5. An elution solution containing counterion and a higher concentration of organic solvent is prepared and placed in the chamber 170. The concentration of organic solvent is calculated to be the amount which will remove a targeted fraction of mRNA molecules from the separation medium. In some instances, it will be desirable to use a concentration of organic solvent that is low enough to cause non-target molecules with greater affinity for separation medium than the targeted mRNAs to remain bound to the column, thereby effectively separating these molecules from target mRNAs.

6. The separation device is centrifuged until all of the free elution solution has passed into the chamber 172. The inner cylinder 144 is removed from the vial, and the contents of chamber 172, containing purified targeted RNA molecule or molecules, is removed for further processing.

Obviously, vial 142 can be replaced between steps or cleaned between steps to prevent contamination of the product fraction or fractions.

The concentration of organic solvent in the elution solution can be selected to remove a single polynucleotide species or a plurality of polynucleotides sharing similar physical characteristics and hence affinity for the separation medium.

Steps (5) and (6) can be repeated with successively higher concentrations of organic solvent to remove a series of polynucleotide-containing fractions.

It will be readily apparent to a person skilled in the art that other variations can be applied to remove a one or a series of purified fractions in much the same manner as described above.

Figure 4:
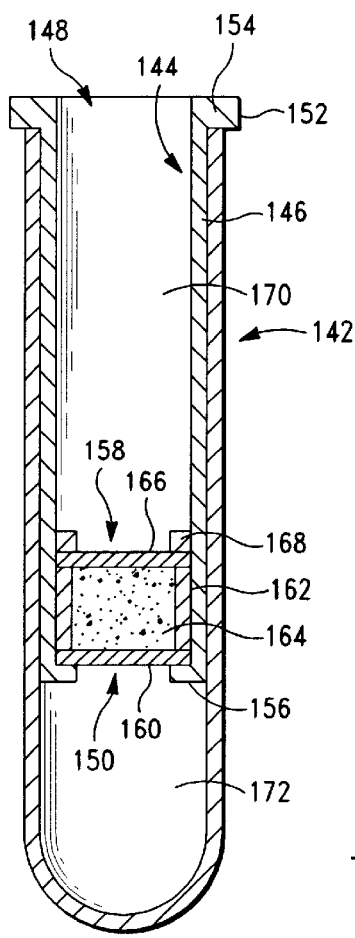
FIG. 4 is a cross-sectional representation of a spin vial system suitable for performing IP-RPC separations.
Figure 5:
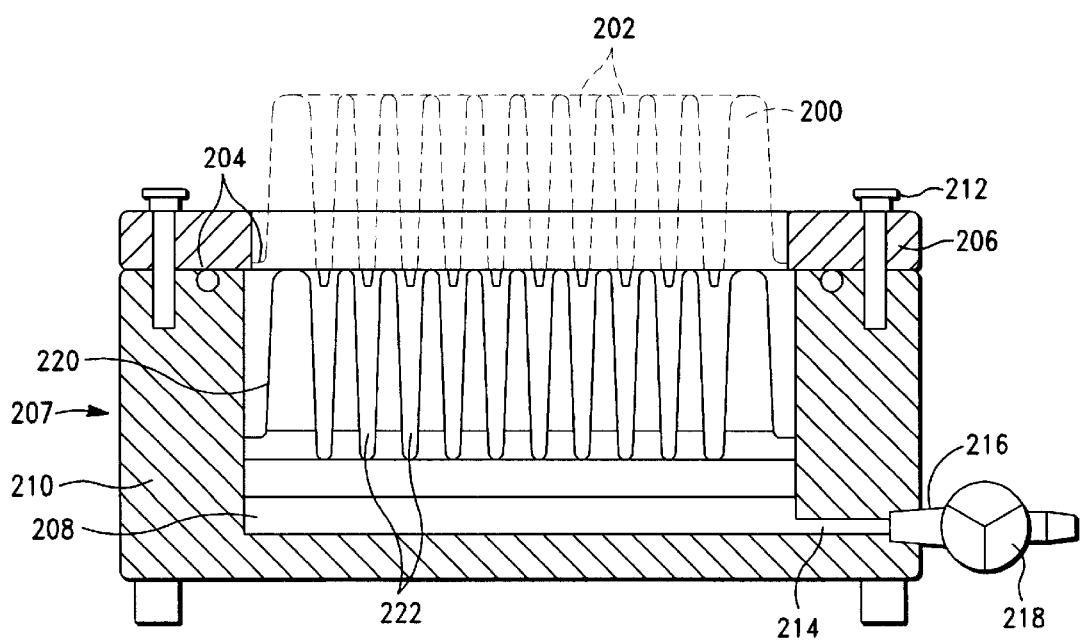
FIG. 5 is a multiwell plate separation system of this invention in combination with a vacuum attachment.

In another embodiment of the invention, separation is achieved by means of a vacuum tray separation device. FIG. 4 is a cross-sectional view of a vacuum tray separation device suitable for use in this invention, and FIG. 5 is a top view of the separation tray of FIG. 4. The separator tray 200 is a single plate with rows and columns of tubular separation channels 202, preferably having regular, repeated spaces between the rows and columns for indexing the spaces. The dimensions of the tray 200 and separation channels can correspond and match the dimensions of standard multi-well plates, such as the 96 cavity microtiter plate.

The multi-channel plate 200 is supported on support flange and vacuum seals 204 formed in the internal cavity of an upper plate 206 of the vacuum assembly 207. The vacuum assembly 207 further comprises a vacuum cavity 208 defined by housing 210. The upper plate 206 positioned on the housing 210 by locating pins 212, and the upper plate 206 and the housing 210 have a sealed engagement with the seals 204. The housing 210 has an exhaust outlet channel 214 communicating with the vacuum chamber 208 and with a vacuum conduit 216 and vacuum valve 218. The vacuum conduit 216 and vacuum valve 218 communicate with a vacuum source (not shown).

A multi-well collection plate 220 is supported in the vacuum chamber 208. The multi-well collection plate 220 is a single plate with rows and columns of separation channels 222, preferably having regular, repeated spaces between the rows and columns for indexing the spaces. The dimensions of the tray 220 and collection channels can correspond and match the dimensions of standard multi-well plates, such as the 96 cavity microtiter plate. The collection plate 220 is held in a position which aligns each of the collection wells 222 with a corresponding separating channel 202 of the separation plate 200 so each well 222 can collect liquid falling from the corresponding separation channel 202.

Figure 6:
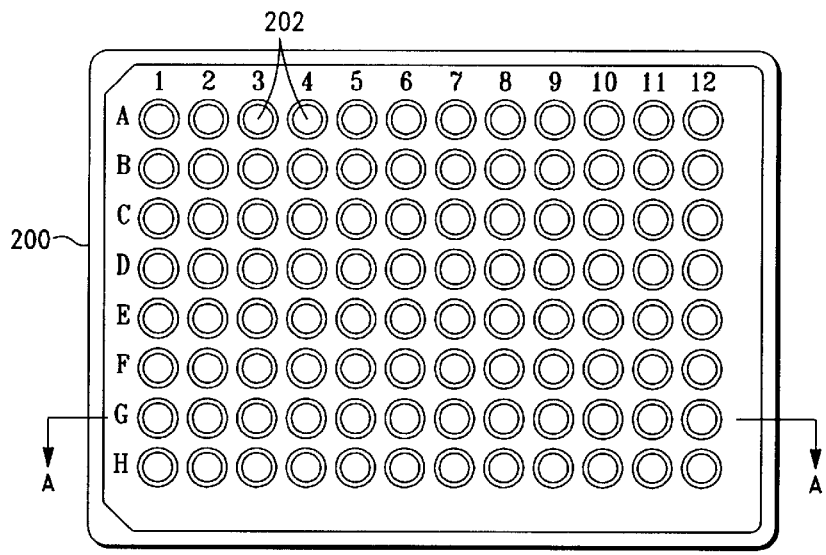
FIG. 6 is the top view of a multiwell plate of FIG. 5.

FIG. 6 is a cross-sectional view of the separation tray of FIG. 4 taken along the line A—A. The separation channels 202 each have an evenly spaced upper cavity 224, separation media 226 and a liquid outlet 228.

Figure 7:
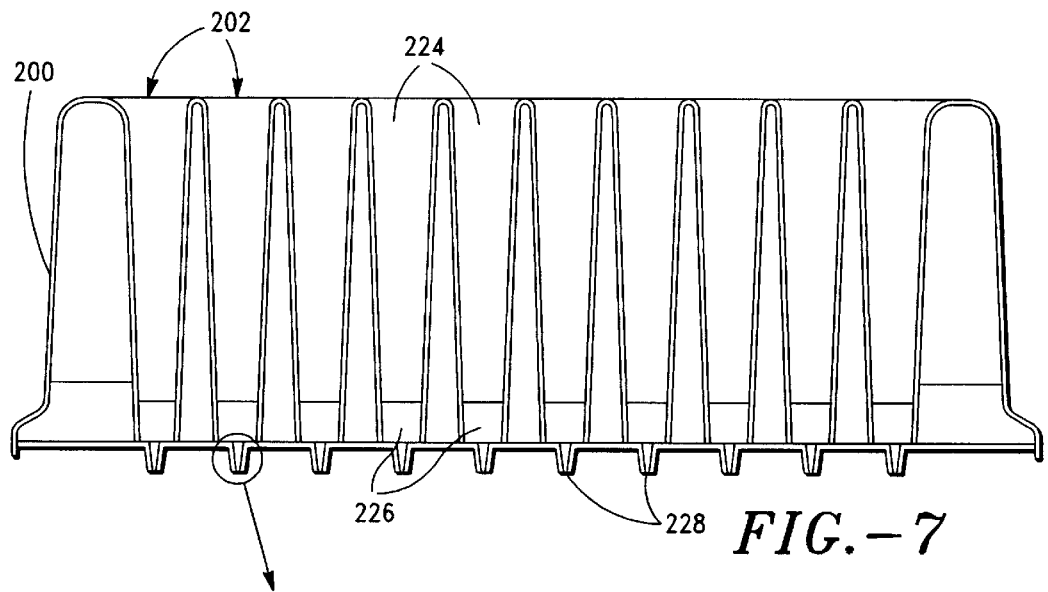
FIG. 7 is a cross-sectional view of the separation tray of FIG. 5 taken along the line A—A.
Figure 8:
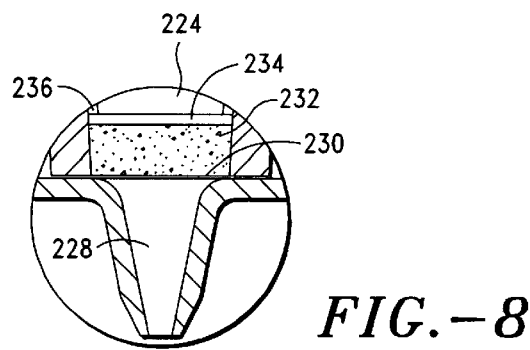
FIG. 8 is an enlarged view of a single separation cell of the multiwell plate of FIG. 7.

FIG. 7 is an enlarged view of the separation components of the separation tray of FIG. 6. The bottom of the separation cavity 224 supports a porous disk 230, which in turn supports separation medium 232. An optional containment disk 234 rests on the separation media 232, and the containment disk 234 can be optionally held in place by friction ring 236 or an equivalent device.

The separation medium 232 is of the type described above.

The separation of polynucleotides using the device of FIGS. 4–7 can be achieved by the following sequence of steps.

1) A solution containing the mRNA molecules of interest is diluted in a loading solution containing an appropriate counterion agent and no organic solvent, or a concentration of organic solvent below that which is required to cause elution of mRNAs of a desired relative size range.

2) The diluted solution is placed in one of the chambers 202 of the fully assembled vacuum device. The other chambers 202 are filled with other mRNA-containing solutions to be separated by the same procedure.

3) Vacuum is applied to the vacuum chamber 208 by opening vacuum valve 218 until all of the liquid from the mixtures contained in each chamber has collected in chambers 222. The vacuum device is disassembled, and the contents of chambers 222 are discarded. The mRNA molecules to be separated bind to the separation medium 232 in each chamber 202 in this step.

4) The vacuum apparatus and plates are reassembled, and a wash solution containing counterion and an organic solvent is added to the chambers 202. The organic solvent concentration is calculated to be the amount which will remove non-targeted molecules that have less affinity for the separation medium than the targeted mRNA fraction. The appropriate concentration of organic solvent can be pre-determined as described supra.

5) Vacuum is applied to the vacuum chamber 208 by opening vacuum valve 218 until all of the liquid from the mixtures contained in each chamber has collected in chambers 222. The vacuum device is disassembled, and the contents of chambers 222 are removed This step removes from the separation medium contaminants and other non-targeted molecules that have less affinity for the separation medium than the members of the targeted mRNA fraction.

6) The vacuum apparatus and plates are reassembled, and an elution solution containing counterion and an organic solvent is placed in the chambers 202. The concentration of organic solvent is calculated to be the amount which will remove targeted mRNAs from the separation medium. In some instances, it will be desirable to use a concentration of organic solvent that is low enough to cause non-target molecules with greater affinity for separation medium than the target mRNAs to remain bound to the column, thereby effectively separating these molecules from target mRNAs.

7) Vacuum is applied to the vacuum chamber 208 by opening vacuum valve 218 until the liquid from the mixtures contained in each chamber has collected in chambers 222. The vacuum device is disassembled, and the contents of chambers 222, containing the targeted fraction of mRNA molecules, is removed for further processing.

Obviously, the plate 220 can be replaced between steps or cleaned between steps to prevent contamination of the product fraction or fractions.

Steps (6) and (7) can be repeated with successively higher concentrations of organic solvent to remove a series of mRNA fractions.

It will be readily apparent to a person skilled in the art that other variations can be applied to remove a one or a series of purified fractions in much the same manner as described above.

The spin column components 142 and 146 of FIG. 3 and the plates 200 and 220 in FIGS. 4–7 are made of a material which does not interfere with the separation process such as polystyrene, polypropylene, or polycarbonate. The upper plate 206 and housing 210 can be made of any materials having the requisite strength such as a rigid organic polymer, aluminum, stainless steel or the like. The vacuum chamber walls are preferably coated with Teflon film. The vacuum conduit and valve can also be made of Teflon coated aluminum or the like.

In the practice of the instant invention, a population of mRNA molecules is separated by IP-RPC in order to obtain a fraction of mRNA molecules that is enriched for mRNA molecules of a desired size range relative to the population of RNA molecules applied to the column. The fraction is collected as it elutes from the column, either manually or by some form of automated fraction collection. In some embodiments of the invention the fraction is subjected directly to further processing. In a preferred embodiment of the invention, the RNA in the fraction is precipitated from the mobile phase in which it has eluted and then reconstituted in, for example, DEPC-treated water prior to further processing steps.

In the instant invention IP-RP-HPLC is used to fractionate messenger RNA (mRNA). IP-RP-HPLC fractionated mRNA species, which have been shown to exhibit enhanced stability (Azarani et al. and Azarani and Hecker) can then be used for the construction of cDNA libraries enriched for inserts of a desired relative size range, e.g., larger-size insert (>10 kb) cDNA libraries. The instant invention facilitates the isolation, identification, and the cloning of large, full-length genes, a process not readily achievable using currently existing technologies.

In general, mRNA samples prepared by currently available technologies comprise messages ranging from a few hundred nucleotides (nts) to greater than 10,000 nts. During the first stage of a cDNA library construction (reverse transcription of this pool of mRNA species), short mRNA fragments tend to be preferentially amplified relative to larger mRNA fragments. One strategy for achieving preferential transcription and amplification of longer mRNA fragments would be to size fractionate a pool of mRNA molecules to enrich for longer molecule. However, currently existing RNA fractionation techniques such as gel electrophoresis (using highly toxic denaturing agents such as methylmercuric hydroxide or glyoxal and dimethyl sulfoxide; or formaldehyde) or centrifugation through sucrose gradients (containing methylmercuric hydroxide) do not provide satisfactory results (as described, for example, in Sambrook, J., Fritsch, E. F., and Maniatis, T. Molecular Cloning: A laboratory Manual. 2nd Ed., Chapter 7 and 8, Cold Spring Harbor Laboratory Press, Cold Spring Harbor, N.Y. (1989)). In addition to being laborious and lengthy, these techniques potentially modify and subject the RNA samples to degradation by the activity of endogenous as well as exogenous ribonucleases.

Because of the limitation associated with mRNA fractionation by gel electrophoresis and centrifugation through sucrose gradient, some researchers have approached this issue from another angle. One approach involves reverse transcription of non-fractionated mRNA samples, followed by construction of the second-strand, addition of adapters, and PCR amplification of the cDNAs created. These cDNAs are then size fractionated on an agarose gel. The larger amplified fragments are then cut from the gel, purified, and cloned into the appropriate vectors. In another procedure the cDNAs synthesized are directly size fractionated on an agarose gel without the PCR amplification step. While both procedures have resulted in larger insert cDNA libraries (between 400 bp to 5 kb fragments), as reported in Sambrook et al.; Wilcox & Fex (1992) Hear Res. 62, 124–6; Wilcox & Fex (1994) Hear Res 73, 65–6; and Ohara et al. (1997) DNA Res. 4, 53–9, there remains a demand for a technique able to generate even larger fragment. Furthermore, inherent in these procedures are a number of technical disadvantages. For example, both procedures are long and cumbersome. The first procedure increases the chances of introducing mutations in the amplified cDNA fragments during the PCR step, while the second procedure (by avoiding the PCR step) produces a low yield of synthesized cDNA, which results in inefficient gel detection and purification of the cDNA fragments created. Furthermore, since in both procedures the starting mRNA sample contains a pool of messages (ranging from few hundred to few thousand nts), all competing to be reverse transcribed, the yield and the sizes of amplified messages are not as efficient as those obtained using the fractionation method of the instant invention, as demonstrated below.

As described above, IP-RP-HPLC represents superior method of RNA analysis. This technology has shown to not only provide detailed information regarding the integrity of RNA samples, but also to stabilize RNA and thus facilitate downstream applications such as reverse transcription (U.S. patent application Ser. No. 09/557,424, Azarani et al. (2000) *Miami Nature Biotechnology Short Reports* 11, 29 and Azarani & Hecker RNA analysis by ion-pair reversed-phase high performance liquid chromatography. *Nucleic Acids Research* (2000) (submitted). In the instant invention, the technology is extended to the size-based fractionation of mRNA and the preparation of cDNA libraries.

As demonstrated herein, RNA derived from different species and organs can be efficiently size-fractionated by IP-RP-HPLC. For example, a sample of human fetal liver mRNA (5 $\mu$g), was fractionated using this technology, as shown in Example 1 and FIG. 1. These fractions were reverse transcribed to form double stranded cDNA that was subsequently cloned into an appropriate vector, as described in Examples 2 and 3. Prior to cloning, a small portion of each fraction was amplified by PCR and analyzed by agarose gel electrophoresis to assess the size of the fragments created. The result, shown in FIG. 2A, demonstrates that the starting mRNA sample is size fractionated into fragments ranging between 500 to higher than 10000 nts. While in fraction 10 (10 minutes into the run) the cDNA fragments amplified are mainly in the 500 bp range, in fraction 11 the majority of amplified cDNAs are in the 1000 bp range. Fraction 12 contains amplified cDNAs in the range of 3000 to 10000 bp. The largest amplified fragments are in fractions 13, 14 and 15 in which cDNAs larger than 10 kb are observed.

Figures 2A, 2B:
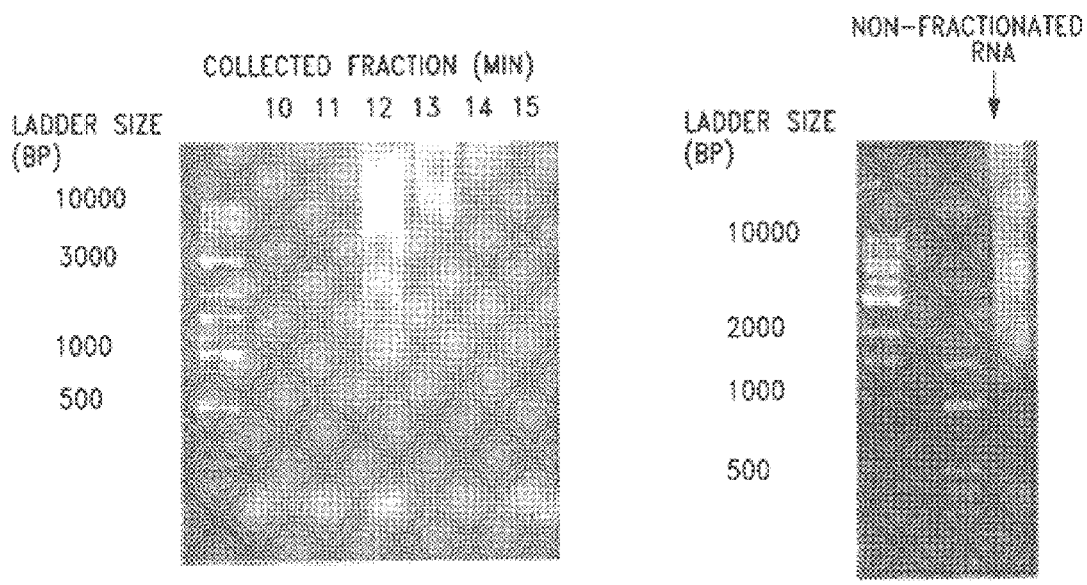
FIGS. 2A And 2B illustrates the difference in size and quantity of cDNA inserts synthesized from IP-RP-HPLC fractionated mRNA (FIG. 2A) compared to non-fractionated mRNA (FIG. 2B), as described in the Examples. In both experiments DNA ladders were used to show the approximate sizes of the cDNA fragments synthesized.

Furthermore, the yield and sizes of amplified messages obtained by fractionation according to the instant invention are more efficient than can be achieved using the alternative methods described above. This is illustrated in FIG. 2B, wherein 5 $\mu$g of non-fractionated human fetal liver mRNA was reverse transcribed and turned into double-stranded cDNA. The cDNAs created were PCR amplified and analyzed on an agarose gel. While a range of cDNA fragments are amplified, the majority of these fragments are between 1500 to 5000 bp (FIG. 2B). This comparison clearly indicates that fractionation results in more effective reverse transcription and subsequent amplification of large size mRNA species. In practice of the invention, a selected fraction of IP-RPC fractionated mRNA can be converted into double-stranded cDNA by reverse transcription using any of a variety of techniques well known in the art, as described, for example in Ausubel and Sambrook. In a preferred embodiment of the invention, cDNA is synthesized from the RNA templates by reverse transcription followed by the polymerase chain reaction (RT-PCR). In RT-PCR, the RNA template is first copied into cDNA using a reverse transcriptase (RTase), a reaction termed "first strand synthesis." RT reactions can be primed with random primers, oligo(dT), or a gene-specific primer (GSP). The RT reaction is preferably accomplished under conditions that disrupt RNA secondary structure. This can be achieved, for example, by running the reaction at higher temperature or by the inclusion of additives such as glycerol and DMSO.

Following reverse transcription, PCR is performed to exponentially amplify the cDNA. RT-PCR protocols fall into several categories based on the number of enzymes used and whether the reverse transcription and PCR components of the procedure are performed separately. In two-step RT-PCR, each step is performed under optimal conditions. cDNA synthesis is performed in RT buffer and one tenth of the reaction is removed for PCR. In one-step RT-PCR, reverse transcription and PCR take place sequentially in a single tube under conditions optimized for both RT and PCR. In a preferred embodiment of the invention, a RTase with attenuated RNAse H activity, such as the genetically engineered RTases SuperScript™ and ThermoScript™, both available from Life Technologies (New York, N.Y.) are used. An additional attribute of ThermoScript™ is that the enzyme has been engineered to have high thermal stability, allowing first strand synthesis to be performed at 50° C. to 65° C., which is desirable in certain embodiments of the instant invention. In a preferred embodiment of the invention, cDNA inserts prepared according to the instant invention are inserted into an appropriate nucleic acid vector, e.g., a plasmid, phage (lambda), phagemid, cosmid or other suitable vector that can be replicated in a prokaryotic and/or eukaryotic host. Non limiting examples include the plasmid vector CDM8 (Invitrogen), and Lambda vectors λgt10, λgt11, EMBL 3 or 4, Charon 4A, Uni-ZAP® XR (Stratagene, La Jolla, Calif.)., Lambda ZAP®-CMV (Stratagene), ZAP Express® (Stratagene) or HybriZAP® 2.1(Stratagene) vectors. A preferred vector for use in the instant invention is the ZAP Express® Vector, available from Stratagene (ZAP Express kit, catolog no. 239211). In many cases it will be necessary to ligate an appropriate linker or adapter to the cDNA to enable it to be cloned into the vector. This can be accomplished using techniques well known in the art, as described for example in Ausubel and Sambrook. Libraries can be prepared in either a random or directional manner, as appropriate.

In a preferred embodiment of the invention, the cDNA library resides in a suitable host cell, which can be either prokaryotic or eukaryotic. Introduciton of cDNA-containing vector DNA into a host cell can be accomplished by any of a variety of techniques well known in the art, including transfection, transformation, electroporation, etc. Non-limiting examples of suitable host cells (for use with the appropriate vectors) include E. coli strains C600hflA, Y1088, P2392, Q359, NM539, LE392MC1061/P3 (Invitrogen), CDM8, MC1061, DK1, DH1, DH5 and HB101. A preferred host cell is XL1-Blue MRF', included with the Stratagene ZAP Express Kit, catalog no. 239211.

A major problem often faced during the construction of large-insert cDNA libraries is the difficulty of successful cloning of the various cDNA fragments created. It has been shown, for example, that when a pool of restriction fragments differing in length by an order of magnitude were ligated into a plasmid vector, the smaller fragments were selectively cloned (Matin & Hornby (2000) Anal. Biochem. 278:46–51). This is a commonly observed phenomenon in the construction of complex DNA libraries (Sambrook et al.). Since the majority of the fragments created by the use of non-fractionated mRNA samples fall in the range of 1000 to 5000 bp, there is less of a chance to incorporate the smaller population of larger (>5 kb) cDNA fragments created. However, mRNA fractionation according to the instant invention eliminates this problem by enriching for longer fragments. Since fractionated fragments are mostly within the same size range, cloning competition between very different size fragments is decreased and the chances of cloning specific size (especially larger) fragments are increased.

Another significant advantage of mRNA fractionation by IP-RP-HPLC technology is that fractionated mRNA samples are more stable compared to non-fractionated samples, as previously described in Azarani et al. and Azarani and Hecker. This is shown in Example 4, Table 1 A and 1 B, wherein RNA stability was assessed by β-actin gene specific RT-PCR on both fractionated and non-fractionated mouse brain mRNA samples. In these experiments, the amount of the β-actin RT-PCR product produced from the RNA samples on day zero is set to 100%. The RT-PCR was repeated at different times on stored samples and the amount of the β-actin produced was compared to that of day zero. While IP RP HPLC fractionated RNA samples kept at room temperature for a period of a month showed less than 25% reduction in the amount of RT-PCR product, non-fractionated RNA samples kept under the same conditions were completely degraded. Without intending to be bound by any particular theory, it is believed this phenomenon occurs, at least in part, as a result of the isolation of RNA molecules away from proteins (e.g., ribonucleases) capable of degrading RNA. Thus the collected RNA samples exhibit higher stability and result in more successful RT-PCR results.

Gene specific RT-PCR studies were performed on various mRNA samples (different species and organs) to determine the effect of mRNA fractionation on the recovery of different size and copy messages, as described in Example 5. Results are reported in Table 2. Different size low, medium, and high copy number genes were successfully reverse transcribed and amplified from IP-RP HPLC fractionated mRNA samples. These results clearly indicate that rare, low copy species of mRNA such as p53, in addition to being very stable during the fractionation procedures, are highly recoverable. While the majority of these messages were eluted in more than one fraction, the elution fraction marked in Table 2 indicates the one resulting in the highest amount of product reverse transcribed. For most mRNA species, the larger the size of the message the later it was eluted from the column. However, few exceptions are observed such as in the case of IL-8 with a message size of 1253 nts having the same elution time as ILGF-1 with a message size of 7260 nts.

In conclusion, in addition to its numerous unique RNA and DNA applications, the IP RP HPLC technology allows for the successful fractionation of mRNA species, thereby facilitating the capturing and isolation of especially longer, full-length genes. The mRNA samples fractionated are highly stable during the fractionation and result in more successful RT-PCR products. This technology also allows the successful cloning of rare, low copy genes.

Other features of the invention will become apparent in the course of the following descriptions of exemplary embodiments which are given for illustration of the invention and are not intended to be limiting thereof. Standard molecular biology techniques such as ligation, restriction digestions, gel electrophoresis and cloning were used in the following examples, using standard methods well known in the art and described, for example, in Sambrook and Ausubel.

Procedures described in the past tense in the examples below have been carried out in the laboratory. Procedures described in the present tense have not yet been carried out in the laboratory, and are constructively reduced to practice with the filing of this application. All references referred to herein, including any patent, patent application or non-patent publication, are hereby incorporated by reference in their entirety.

EXAMPLE 1

Fractionation of Human Fetal Liver mRNA

A 5 µg sample of human fetal liver mRNA (Clontech, Palo Alto, Calif.) (Cat. No. 6527–1) was separated by IP-RP-HPLC on a DNASep chromatography cartridge (7.8 mm internal diameter and 50 mm length; Transgenomic, Inc.) using a WAVE Nucleic Acid Fragment Analysis System (Transgenomic, Inc., San Jose, Calif.). The stationary phase of the cartridge comprises a nonporous, C-18 alkylated poly(styrene-divinylbenzene) separation medium.

Chromatography was performed using a two-eluent buffer system. All eluants and buffers were made using DEPC-treated, double distilled deionized water, and precautions were taken to maintain a chromatography environment free of metal ions that could interfere with RNA separation. Buffer A consists of an aqueous solution of 0.1 M triethylammonium acetate (TEAA) (pH 7.0) and buffer B consists of an aqueous solution of 0.1 M TEAA (pH 7.0) with 25% (v/v) of acetonitrile (ACN) (TEAA provided by Transgenomic, Inc., San Jose, Calif.). The separation was performed under fully denaturing conditions at 75° C. Chromatograms were recorded at a wavelength of 260 nm. The following gradient was used: flow rate 0.9 mL/min, 38 to 40% B in 1.0 min, to 60% B in 15 min, to 66% B in 6.0 min, to 70% B in 0.5 min, to 100% B in 0.5 min, hold at 100% B for 1 min, to 38% B in 1 min, hold at 38% B for 2 min. The resulting chromatogram is shown in FIG. 1.

EXAMPLE 2 cDNA Library Construction

Starting 6 minutes into the separation run described in Example 1, when mRNA species started to separate and resolve, 1-min fractions (0.9 ml) were collected, precipitated, and reconstituted in 5 µl of DEPC-treated water. Precipitation of eluted RNA samples was performed by addition of 10% (v/v) of precipitation buffer (10 mM Tris-HCl (pH 7.0), 1 mM EDTA, 3.0 M NaCl), 1% (v/v) of glycogen (10 mg/mL), and 2.5 volumes of ethanol. Samples were kept at −70° C. for 10 min or at −20° C. for two hours before centrifugation at 13,000 g for 15 min at 4° C.

The reconstituted fractions were reverse transcribed using oligo(dT) primers and the ThermoScript™ RT-PCR kit (Life Technologies, New York, N.Y.; Cat. No. 11146–040) according to the manufacturer's instruction included with the kit. Second-strand synthesis was accomplished by nick translational replacement of the mRNA using the SuperScript™ Lambda System (Life technologies; Cat. No. 19643-014). EcoR I adapters (Stratagene, Calif.) were ligated to the ends of the double stranded cDNAs.

EXAMPLE 3 cDNA Analysis

A small portion of the double stranded cDNA samples from Example 2 were PCR amplified by specific primers complementary to the EcoR I adapters. The samples were analyzed by 1% agarose gel electrophoresis to assess the size of the fragments created. The results, shown in FIG. 2A, show that the starting mRNA sample is size fractionated into fragments ranging between 500 to higher than 10,000 nts. While in fraction 10 (10 minutes into the run) the cDNA fragments amplified are mainly in the 500 bp range, in fraction 11 the majority of amplified cDNAs are in the 1000 bp range. Fraction 12 contains amplified cDNAs in the range of 3000 to 10000 bp. The largest amplified fragments are in fractions 13, 14 and 15 in which cDNAs larger than 10 kb are observed.

For comparison, the above experiment was repeated using 5 µg of non-fractionated human fetal liver mRNA. The cDNAs created were PCR amplified and analyzed on an agarose gel, shown in FIG. 2B. While a range of cDNA fragments are amplified, the majority of these fragments are between 1500 to 5000 bp. This comparison clearly indicates that fractionation results in more effective reverse transcription and subsequent amplification of large size mRNA species.

EXAMPLE 4

Assessment of RNA Stability

RNA stability was assessed by β-actin gene specific RT-PCR on both fractionated and non-fractionated (6–15 minute fractions were used) mouse brain mRNA samples (Clontech Inc., Palo Alto, Calif.). 5 out of the original 900 µl of original mRNA samples were reverse transcribed and amplified by RT-PCR, as described above, using β-actin gene specific primers obtained from Clontech. In these experiments, the amount of the β-actin RT-PCR product produced from the RNA samples on day zero is set to 100%. Quantification was achieved by IP-RP-HPLC of the RT-PCR product and integration of the area under the chromatogram peak corresponding to the reverse transcript of interest. IP-RP-HPLC and detection was performed as described above. A conversion factor, which is a function of flow rate, was used based on the relationship between peak area and a known amount of DNA analyzed.

The RT-PCR was repeated at different times on stored samples (stored at either room temperature (RT) or at −20° C.) and the amount of the β-actin produced was compared to that of day zero, as shown in Tables 1A and 1 B. While IP-RP-HPLC fractionated RNA samples kept at room temperature for a period of a month showed less than 25% reduction in the amount of RT-PCR product, non-fractionated RNA samples kept under the same conditions were completely degraded.

TABLE 1A

| % β-actin produced | Day 0 | One month |
|---|---|---|
| At RT | 100% | 77% |
| At −20 | 100% | 100% |

TABLE 1B

| % b-actin produced | Day 0 | One month |
|---|---|---|
| At RT | 100% | 0% |
| At −20 | 100% | 14% |

EXAMPLE 5

Gene Specific RT-PCR Studies

Gene specific RT-PCR studies were performed on mRNA samples (mouse brain mRNA and/or human fetal liver mRNA; 5 µg was loaded onto the column) to determine the effect of mRNA fractionation on the recovery of different size and copy messages. Results are reported in Table 2. The amplicon size is shown in bold and the mRNA size for each gene is indicated in parentheses. The level of the expression of each gene is indicated in terms of low, medium and high copy. Abbreviations used are: ILGF-1 for insulin-like growth factor I, IGFR-1 for insulin-like growth factor receptor type I, EGFR-3 for epidermal growth factor receptor type 3, MHC I for major histocompatibility complex class I, IL-8 for interleukin-8. Different size low, medium, and high copy number genes were successfully reverse transcribed and amplified (by RT-PCR as described above, using gene specific primers purchased from Clontech) from IP-RP-HPLC fractionated mRNA samples (6–15 min fractions were individually analyzed for each transcript). While the majority of these messages was eluted in more than one fraction, the elution fraction marked in Table 2 indicates the one resulting in the highest amount of product reverse transcribed, based on quantification by IP-RP-HPLC as described in Example 4. These results clearly indicate that rare, low copy species of mRNA such as p53, in addition to being very stable during the fractionation procedures, are highly recoverable. For most mRNA species, the larger the size of the message the later it was eluted from the column. However, a few exceptions are observed such as in the case of IL-8 with a message size of 1253 nts having the same elution time as ILGF-1 with a message size of 7260 nts. Single-stranded nucleic acid molecules with high adenine content exhibit longer retention times compared to those with high guanine or cytosine content. The (A+T)/(C+G) ratios for the mRNA species amplified in this study are reported in Table 2. The close (A+T)/(C+G) ratios calculated for IL-8 and ILGF-1 (1.8 and 1.7, respectively), therefore, predict the observed similar elution patterns for both messages. However, even though few mRNA species (with high A and T contents) show exceptional elution patterns, most mRNA species are fractionated according to their size as is apparent from results in FIG. 2A and Table 2.

TABLE 2

| Transcript | 6 min | 7 min | 8 min | 9 min | 10 min | 11 min | 12 min | 13 min | 14 min | 15 min | (A + T)/(C + G) |
|---|---|---|---|---|---|---|---|---|---|---|---|
| ILGF-1 514 (7260) Low copy | | | | | | | | X | | | 1.7 |
| IGFR-1 540 (4989) Low copy | | | | | | X | | | | | 0.9 |
| EGFR-3 675 (4879) Low copy | | | | | | X | | | | | 0.9 |
| β-actin 1716 (1761) High copy | | | | X | | | | | | | 0.8 |
| α-tubulin 527 (1596) Low copy | | | | | | X | | | | | 0.9 |
| MHC-I 566 (1413) Low copy | | | | | | X | | | | | 0.7 |
| P 53 1182 (1307) Low copy | | | | X | | | | | | | 0.8 |
| IL-8 289 (1253) Med copy | | | | | | | | | X | | 1.8 |

EXAMPLE 6

Fractionation of RNA on a Silica-based Separation Medium

A 2 µg sample of an RNA ladder (0/155–1.77 kb) (Life Technologies, Rockville, Md.) (Cat. No. 6527–1) was separated by IP-RP-HPLC on an Eclipse dsDNA Analysis Column (4.6 mm internal diameter and 75 mm length; Agilent Technologies, Wilmington, Del.) using a WAVE Nucleic Acid Fragment Analysis System (Transgenomic, Inc., San Jose, Calif.). The stationary phase of the cartridge comprises porous 3.5 micron silica-based beads.

Chromatography was performed using a two-eluent buffer system. All eluants and buffers were made using DEPC-treated, double distilled deionized water, and precautions were taken to maintain a chromatography environment free of metal ions that could interfere with RNA separation. Buffer A consists of an aqueous solution of 0.1 M triethylammonium acetate (TEAA), 0.1 mM EDTA (pH 7.0) and buffer B consists of an aqueous solution of 0.1 M TEAA (pH 7.0), 0.1 mM EDTA with 25% (v/v) of acetonitrile (ACN) (TEAA provided by Transgenomic, Inc., San Jose, Calif.). Separations were performed at 50° C., 65° C., and 75° C. Chromatograms were recorded at a wavelength of 260 nm. The following gradient was used: flow rate 0.9 mL/min, 38 to 40% B in 1.0 min, to 60% B in 15 min, to 66% B in 6.0 min, to 70% B in 0.5 min, to 100% B in 0.5 min, hold at 100% B for 1 min, to 38% B in 1 min, hold at 38% B for 2 min. The resulting chromatograms are shown in FIG. 3 (3A: 50° C.; 3B: 65° C.; and 3C: 75° C.).

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A method for preparing a fraction of mRNA molecules suitable for use in the production of a cDNA library enriched for inserts of a desired relative size range comprising the steps of:
   a) applying a plurality of mRNA molecules to a separation medium having a non-polar surface in the presence of a counterion agent, wherein said plurality of mRNA molecules comprises mRNA molecules of diverse sizes, wherein said plurality of mRNA molecules has not been exposed to methylmercuric hydroxide;
   b) eluting at least a portion of the plurality of mRNA molecules from the separation medium by means of a mobile phase that includes a solvent that is less polar than water, whereby the plurality of mRNA molecules subjected to separation in a manner that is at least partially dependent upon mRNA size; and
   c) collecting a fraction of mRNA molecules as it elutes from the column, wherein the fraction of mRNA molecules collected is enriched for mRNA molecules of a desired size range relative to the plurality of mRNA molecules applied to the column, such that the fraction of mRNA molecules collected is suitable for use in the production of a cDNA library enriched for inserts of a desired relative size range.

2. The method of claim 1, wherein the fraction of mRNA molecules collected is enriched for the larger-size constituents of the plurality of mRNA molecules applied to the separation medium, wherein said larger-size constituents comprise mRNA molecules of greater than about 5000 bases.

3. The method of claim 2, wherein the library of cDNA inserts comprises cDNA inserts residing in nucleic acid vectors.

4. The method of claim 3, wherein the nucleic acid vectors are selected from the group consisting of phage vectors and plasmids.

5. The method of claim 3, wherein the nucleic acid vectors are contained in host cells.

6. The method of claim 1, wherein the plurality of mRNA molecules applied to the separation medium comprises a sample of total mRNA from a biological sample.

7. The method of claim 2, wherein the plurality of mRNA molecules applied to the separation medium comprises a sample of total RNA from a biological sample.

8. The method of claim 2, wherein the separation of mRNA molecules is achieved by Ion Pairing Reversed Phase HPLC.

9. The method of claim 2, wherein the separation of mRNA molecules is achieved under denaturing conditions.

10. The method of claim 9, wherein mRNA denaturation is achieved by conducting the separation at a temperature sufficient to denature at least some portion of the plurality of mRNA molecules applied to the separation medium.

11. The method of claim 9, wherein mRNA denaturation is achieved by conducting the separation in the presence of a chemical denaturant.

12. The method of claim 9, wherein mRNA denaturation is achieved by conducting the separation at a pH sufficient to denature at least some portion of the plurality of mRNA molecules applied to the separation medium.

13. The method of claim 2, wherein the separation medium comprises particles selected from the group consisting of silica, silica carbide, silica nitrite, titanium oxide, aluminum oxide, zirconium oxide, carbon, insoluble polysaccharide, and diatomaceous earth, the particles having separation surfaces which are coated with a hydrocarbon or non-polar hydrocarbon substituted polymer, or have substantially all polar groups reacted with a non-polar hydrocarbon or substituted hydrocarbon group, wherein the surfaces are non-polar.

14. The method of claim 2, wherein the separation medium comprises polymer beads having an average diameter of 0.5 to 100 microns, the beads being unsubstituted polymer beads or polymer beads substituted with a moiety selected from the group consisting of hydrocarbon having from one to 1,000,000 carbons, wherein said moiety comprises an alkyl group.

15. The method of claim 2, wherein the mobile phase includes an organic solvent selected from the group consisting of alcohol, nitrile, dimethylformamide, tetrahydrofuran, ester, ether, and mixtures thereof.

16. The method of claim 15, wherein the mobile phase includes acetonitrile.

17. The method of claim 2, wherein the mobile phase includes a counterion agent selected from the group consisting of lower alkyl primary amine, lower alkyl secondary amine, lower alkyl tertiary amine, lower trialkylammonium salt, quaternary ammonium salt, and mixtures thereof.

18. A method for preparing a cDNA library enriched for inserts of a desired relative size range comprising the steps of:
   a) applying a plurality of mRNA molecules to a separation medium having a non-polar surface in the presence of a counterion agent, wherein said plurality of mRNA molecules comprises mRNA molecules of diverse sizes, wherein said plurality of mRNA molecules has not been exposed to methylmercuric hydroxide;

b) eluting at least a portion of the plurality of mRNA molecules from the separation medium by applying a mobile phase that includes a solvent that is less polar than water, whereby the plurality of mRNA molecules subjected to separation in a manner that is at least partially dependent upon mRNA size;

c) collecting a fraction of mRNA molecules as it elutes from the column, wherein the fraction of mRNA molecules collected is enriched for mRNA molecules of a desired size range relative to the plurality of mRNA molecules applied to the column; and d) reverse transcribing the collected fraction of mRNA molecules to form a library of cDNA inserts enriched for inserts of a desired relative size range.

19. The method of claim 18, wherein the fraction of mRNA molecules collected is enriched for the larger-size constituents of the plurality of mRNA molecules applied to the separation medium, wherein said larger-size constituents comprise mRNA molecules of greater than about 5000 bases.

20. The method of claim 19, wherein the library of cDNA inserts comprises cDNA inserts residing in nucleic acid vectors.

21. The method of claim 20, wherein the nucleic acid vectors are selected from the group consisting of phage vectors and plasmids.

22. The method of claim 20, wherein the nucleic acid vectors are contained in host cells.

23. The method of claim 18, wherein the plurality of mRNA molecules applied to the separation medium comprises a sample of total mRNA from a biological sample.

24. The method of claim 19, wherein the plurality of mRNA molecules applied to the separation medium comprises a sample of total RNA from a biological sample.

25. The method of claim 19, wherein the separation of mRNA molecules is achieved by Ion Pairing Reversed Phase HPLC.

26. The method of claim 19, wherein the separation of mRNA molecules is achieved under denaturing conditions.

27. The method of claim 26, wherein mRNA denaturation is achieved by conducting the separation at a temperature sufficient to denature at least some portion of the plurality of mRNA molecules applied to the separation medium.

28. The method of claim 26, wherein mRNA denaturation is achieved by conducting the separation in the presence of a chemical denaturant.

29. The method of claim 26, wherein mRNA denaturation is achieved by conducting the separation at a pH sufficient to denature at least some portion of the plurality of mRNA molecules applied to the separation medium.

30. The method of claim 19, wherein the separation medium comprises particles selected from the group consisting of silica, silica carbide, silica nitrite, titanium oxide, aluminum oxide, zirconium oxide, carbon, insoluble polysaccharide, and diatomaceous earth, the particles having separation surfaces which are coated with a hydrocarbon or non-polar hydrocarbon substituted polymer, or have substantially all polar groups reacted with a non-polar hydrocarbon or substituted hydrocarbon group, wherein the surfaces are non-polar.

31. The method of claim 19, wherein the separation medium comprises polymer beads having an average diameter of 0.5 to 100 microns, the beads being unsubstituted polymer beads or polymer beads substituted with a moiety selected from the group consisting of hydrocarbon having from one to 1,000,000 carbons, wherein said moiety comprises an alkyl group.

32. The method of claim 19, wherein the mobile phase includes an organic solvent selected from the group consisting of alcohol, nitrile, dimethylformamide, tetrahydrofuran, ester, ether, and mixtures thereof.

33. The method of claim 32, wherein the mobile phase includes acetonitrile.

34. The method of claim 19, wherein the mobile phase includes a counterion agent selected from the group consisting of lower alkyl primary amine, lower alkyl secondary amine, lower alkyl tertiary amine, lower trialkylammonium salt, quaternary ammonium salt, and mixtures thereof.

* * * * *